US008709426B2

(12) United States Patent
Hercend et al.

(10) Patent No.: US 8,709,426 B2
(45) Date of Patent: Apr. 29, 2014

(54) NUCLEOTIDE SEQUENCE CODING FOR VARIABLE REGIONS OF β CHAINS OF HUMAN T LYMPHOCYTE RECEPTORS, CORRESPONDING PEPTIDE SEGMENTS AND THE DIAGNOSTIC AND THERAPEUTIC USES

(75) Inventors: Thierry Hercend, Nogent-sur-Marne (FR); Frederic Triebel, Neuilly-sur-Seine (FR); Sergio Roman-Roman, Paris (FR); Laurent Ferradini, Paris (FR)

(73) Assignee: Aventis Pharma S.A., Paris (FR)

( * ) Notice: Subject to any disclaimer, the term of this patent is extended or adjusted under 35 U.S.C. 154(b) by 308 days.

(21) Appl. No.: 11/867,862

(22) Filed: Oct. 5, 2007

(65) Prior Publication Data
US 2008/0069770 A1 Mar. 20, 2008

Related U.S. Application Data

(60) Division of application No. 10/095,672, filed on Mar. 12, 2002, now Pat. No. 7,294,712, which is a continuation of application No. 09/103,460, filed on Jun. 24, 1998, now abandoned, which is a division of application No. 08/437,353, filed on May 9, 1995, now Pat. No. 5,830,758, which is a division of application No. 08/423,383, filed on Apr. 14, 1995, now Pat. No. 5,700,907, which is a continuation of application No. 07/934,530, filed on Nov. 23, 1992, now abandoned.

(30) Foreign Application Priority Data

Feb. 12, 1991 (FR) ..................................... 91/01613
Apr. 12, 1991 (FR) ..................................... 91/04523

(51) Int. Cl.
*A61K 39/395* (2006.01)
(52) U.S. Cl.
USPC ............... 424/144.1; 530/388.22; 530/388.75
(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 4,743,679 A | 5/1988 | Cohen et al. | |
| 4,786,590 A * | 11/1988 | McGrath et al. | 424/144.1 |
| 4,886,743 A * | 12/1989 | Hood et al. | 435/5 |
| 5,043,272 A | 8/1991 | Hartley | |
| 5,223,426 A | 6/1993 | Skibbens et al. | |
| 5,665,548 A | 9/1997 | Erlich et al. | |
| 5,700,907 A * | 12/1997 | Hercend et al. | 530/324 |
| 5,705,627 A | 1/1998 | Manos et al. | |
| 5,798,231 A | 8/1998 | Hercend et al. | |
| 5,817,511 A | 10/1998 | Hercend et al. | |
| 5,830,758 A | 11/1998 | Hercend et al. | |
| 5,840,304 A | 11/1998 | Davis et al. | |
| 6,084,087 A | 7/2000 | Friedman et al. | |
| 6,114,516 A | 9/2000 | Hercend et al. | |

FOREIGN PATENT DOCUMENTS

WO    WO 90/04648    5/1990
WO    WO 90/06758    6/1990

OTHER PUBLICATIONS

Kimura et al., J Exp Med. Sep. 1, 1986;164(3):739-50.*
Bost et al., Immunol. Invest. 1988; 17:577-586.*
Harlow et al., Antibodies: A Laboratory Manual, Cold Spring Harbor Laboratory, 1988, pp. 72-78.*
Meuer et al., J Exp Med. Feb. 1, 1983; 157(2): 705-719.*
Agrawal et al., Inhibition of Human Immunodeficiency Virus in Early Infected and Chronically Infected Cells by Antisense Oligodeoxynucleotides and their Phosphorothioate Analogues , PNAS, vol. 86, 1989, pp. 7790-7794.
Chien et al., How αβ T-cell receptors "see" peptide/MHC complexes , Immunology Today,vol. 14, 1993, 597-602.
Choi et al., Interaction of *Staphylococcus aureus* Toxin "Superantigens" with Human T Cells , PNAS, vol. 86, 1989, pp. 8941-8945.
Choi et al., Residues of the variable region of the T-cell-receptor Beta-chain that interact with *S. aureus* toxin superantigens , Nature,vol. 346, 1990, pp. 471-473.
Concannon et al., Diversity and structure of human T-cell receptor beta-chain variable region genes, pp. 66598-6602, PNAS, vol. 83, Sep. 1986, pp. 6598-6602.
Duby et al, Abnormal recombination products result from aberrant DNA rearrangement of the human T-cell antigen receptor beta-chain gene, PNAS, vol. 83, Jul. 1986, pp. 4890-4894.
Ferradini at al., Studies of the human T cell receptor alpha/beta variable region genes II. Identfication of four additional Vbeta subfamilies, Eur. J. of Immunology, vol. 21, No. 4, Apr. 8; 1991, pp. 935-942.
Goverman et al., Basic and Clinical Immunology, ed. By Stites and Terr., Norwalk, CT, 1991, pp. 73-77.
Ikuta et al., Low frequency of somatic Mutation in beta-chain variable region genes of human T-cell receptors, PNAS, vol. 82, No. 22, Nov. 1985, pp. 7701-7705.
Kimura at al., Sequences and repertoire of the human T cell receptor alpha and beta chain variable region genes in thymocytes, European Journal of Immunology, vol. 17, 1987, pp. 375-383.
Leiden et al., Generation of T-lymphooyte receptor for antigen, PNAS; vol. 83, No. 12, Jun. 1986, pp. 4456-4460.
Leiden et al., Immunogentics, vol. 24, 1986, pp. 17-23.

(Continued)

*Primary Examiner* — Zachary Skelding
(74) *Attorney, Agent, or Firm* — Lathrop & Gage LLP; James H. Velema, Esq.

(57) ABSTRACT

The present invention relates to new nucleotide sequences coding for variable regions of β chains of human T lymphocyte receptors, corresponding peptide segments and the diagnostic and therapeutic uses.

11 Claims, 14 Drawing Sheets

(56) References Cited

OTHER PUBLICATIONS

M.A. Robinson, The human T cell receptor beta-chain gene complex contains at least 57 variable gene segment. Identification of six Vbeta genes in four new gene families, J. of Immunology, vol. 146, No. 12, Jun. 12, 1991, pp. 4392-4397.

Plaza et al., New human V beta genes and polymorphic variants, J. of Immunology, vol. 147, No. 12, Dec. 1991, pp. 4360-4365.

Sommer et al., Minimal homology requirements for PCR primers, Nucleic Acids Research, vol. 17, Aug. 1989, p. 6748.

Scottini et al., Restricted expression of T cell receptor Vbeta but not Valpha genes in rheumatoid arthritis, Eur. J. of Immunology, vol. 21, 1991; pp. 461-466.

Sims et al., Complexity of human T-cell antigen receptor beta-chain constant and variable region genes, Nature, vol. 312, Dec. 6, 1984, pp. 541-544.

Smith et al., Germline sequence of two human T-cell receptor Vβ genes: Vβ8.1 is transcribed from a TATA-box promoter, Nucleic Acids Research, vol. 15. No. 12, 1987, p. 4991.

Tillinghast et al., Structure and diversity of the human T-cell receptor beta-chain variable region genes, Science, vol. 233, No. 4766, Aug. 22, 1986, pp. 879-883.

Vandenbark at al., Immunization with a synthetic T-cell receptor V-region peptide protects against experimental autoimmune encephalomyelitis, Nature, vol. 341, 1989, pp. 541-543.

Ayala et al., Modem Genetics, Meno Park, CA, Benjamin/Curnmings Co. 1980.

Concannon, 1986, Genbank. Locus HUMTCYBC, Accession #M13850, M16302.

George, 1990, Genbank Locus HSTVB55, Accession #X56142.

Hinukaneu et al, EMBL/Geubank/DDBR database, Locus: HSTCRBBBC, 1991.

Plaza 1991, Genbank Locus HSV56RNA, Accession #57615.

Plaza et al., EMBL/Geubank/DDBJ database Locus: HSV71RNA 1991.

Plaza, 1991, Genbank Locus HS134BRNA, Accession #57721.

Plaza, 1991, Genbank Locus HSV91RNA, Accaccion #57614.

Plaza, 1991, Genbank. Locus HS22ARNA, Accession #X57725.

Plaza, 1991, Genbank. Locus HSV55RNA, Accession #X57613.

Agrawal et al., Oligodeoxynucleoside phosphoramidates and phosphorothioates as inhibitors of human immunodeficiency virus, PNAS, USA, vol. 85, 1988, pp. 7079-7083.

\* cited by examiner

```
             1
PH27    CAACTTGTGCCCTTTGTCTCCTGTGGACAGGACACATGGATGGATGCTGGAATCACCC
PL4.2
IGRb13               T.........G....----....A.........

100
PH27    AGAGCCCAAGACACAAGGTCACAGAGACAGGAACACCAGTGACTCTGAGATGTCACCA
PL4.2                                  ..........................
IGRb13  ..............A...............GG.AG.....CT..GCG.........

PH27    GACTGAGAACCACCGCTATATGTACTGGTATCGACAAGACCCGGGGCATGGGCTGAGG
PL4.2   ..................C......................................
IGRb13  ....TG.......AA.A......T..................T...A..........

200
PH27    CTGATCCATTACTCATATGGTGTTAAAGATACTGACAAAGGAGAAGTCTCAGATGGCT
PL4.2   ..A.......................................................
IGRb13  ....................C....C...A...........................

PH27    ATAGTGTCTCTAGATCAAAGACAGAGGATTTCCTCCTCACTCTGGAGTCCGCTACCAG
PL4.2   .........................................-...............
IGRb13  .C............C.......CC...C...............T...G..TC

300
PH27    CTCCC-AGACATCTGTGTACTTCTGTGCCATCAGC 324
PL4.2   .....G.....................CT..A 237
IGRb13  .....-........A..T.....C....G...G 294
```

```
IGRb14  AGAAGACCCCTCCATCCTGTAGCACCTGCCATGAGCATCGGGCTCCTGTGCTGTGTGGCCTTTTCTCTCCTGTGGGCAAGTCCAGTGAATGCTGGTGT
IGRb15  ..........TG.T......T.......A..A...................................................G........T...GA.
IGRb16  ..................................aaggcccagccctttccattgggctgcagcatcagctgtttcctctctgcag...........
HBVP34  ...............................................................CA..G..............G.............
CEM     ...........................CG..TT..........................C...........................G........

IGRb14  CACTCAGACCCCAAATTCCAGGTCTCCTGAAGACAGCAGGACATGACACTGCAGTGTGCCCAGGATATGAACCATAAACTCCATGTACTGGTATCGAC
IGRb15  ...C...G.A...C..CT...A....GCAG......G.C..................AGA..A............GA....TG........A....
IGRb16  ........................GCA......T..............................................A..........
HBVP34  .................................................................................G.A.A.....C....
CEM     .....................G...........................................T..............G.A.A..........

IGRb14  AAGACCCAGGGACTGAGGCTGATTTATTACTCAGCTTCTGAGGGTACCACTGACAAAGGAGAAGTCCCAATGGCTACAATGTCTCCAGATTA
IGRb15  .....T.T....AC...G.A.....C..CC...T...AA.A...CA.......G............T..............TG...T.G........GC.
IGRb16  .............G...A...........T..GG..CT....T......T..........C...................C......C.
HBVP34  .............G....................T..GG..CT....T..C......................A....C......G......TG....C.
CEM     .............-G..................................T.................................G......TG........

IGRb14  AACAAACGGGAGTTCTGCTCAGGCTGGAGTCGCTGCTCCCTCCCCCAGAGACATCTGTGTACTTCTGTGCCAGCACC  339
IGRb15  ...C.GAT..T...C.C....C.T..C...T.........TA....T...................................GT  339
IGRb16  .C..C.GA..T..C...........T...............CT..................................................GT  345
HBVP34  .C..C.GA..T..C..........................CT...................................................GT  339
CEM     ..A....A.A.T...CT...GG..T.........................A.........................................G.  339
```

```
        1
IGRb17 GACCCCAGTCAGAGGCCCATCTCAGACCCGAGGCTAGCATGGGCTGCAGGCTGCTCTGTGTGCGGTTCTCTGTCTCCTGGGAGCGGTCCCCATGGAAA
IGRb18 ................................................................C...................................
IGRb19 ..........................................................................................A..T......A..C.

100
IGRb17 CGGGAGTTACGCAGAGACACCAAGAGACACCTGGTCATGGGAATGACAAATAAGAAGTCTTTGAAATGTGAACAACATCTGGGGCATAACGCTATGTATTGGTA
IGRb18 ..........................................................................................T.........
IGRb19 ..T.A.........C..........A.............................................................A......C.GG.....
PL4.9  .............................................................................................A......C.GG..A....

200
IGRb17 CAAGCAAAGTGCTAAGAAGCCACTGGAGCTCATGTTTGTCTACAACTTTAAAGAACAGAAAACAGTGAAAACAACAGTGTGCCAAGTCGCTTCTCACCTGAATGC
IGRb18 .............................................GTC..G.......G.GT.............................T.CGCT.C..G........
PL4.19 ..............................................................................................T.CGCT.C..G........
IGRb19 ...............G.AA..........................C..............G..A.G.GA...TCT..AT...TG.A..............
VPL4.9 ...............G.AA..........................C..............G..A.G.GA...TCT..AT...TG.A..............

300
IGRb17 CCCAACAGCTCTCACTTATGCCTTCACCTACACACCCTGCAGCCAGAAGACTCGGCCCTGTATCTCTGTGCCAGCACC 339
IGRb18 ............................C.....................................C........G. 339
PL4.19 ............................T.....................................C........G. 108
IGRb19 ..........................AA.............G..............A.........C........G. 339
PL4.9  ...T......................AA.............G..............A.........C........G. 255
```

IGRb20 ATCCTGCCCTGGGCCTTGCCTGGTCTGCTCACTCTGCCACTCTGCTGGGCCATGGGCTGCAGGGCTCCTCCTGCTGTGTGGTCTTCTGCTCCTCCAAGCAGTCCCTTGGACA
        1                                                                                                    100

IGRb20 CAGCTGTTTCCCAGACTCCAAAATACCTGGTCACACAGATGGGAAACGACAAGTCCATTAAATGTGAACAAAATCTGGCCATGATACTATGTATTGGTA
PL2.6  .........................................G..T..........................................................
                                                                                                    200

IGRb20 TAAACAGGACTCTAAGAAATTTCTGAAGATAATGTTTAGCTACAATAATAAGGAGCTCATTATAAATGAAACAGTTCCAAATCGCTTCTCACCTAAATCT
PL2.6  ........................................................................................................
                                                                                                    300

IGRb20 CCAGACAAAGCTCACTTAAATCTTCACATCAATTCCCTGGAGCTTGGTGACTCTGCTGTGTATTTCTGTGCCAGCAGC  339
PL2.6  ...........................................................................  246

FIG. 6

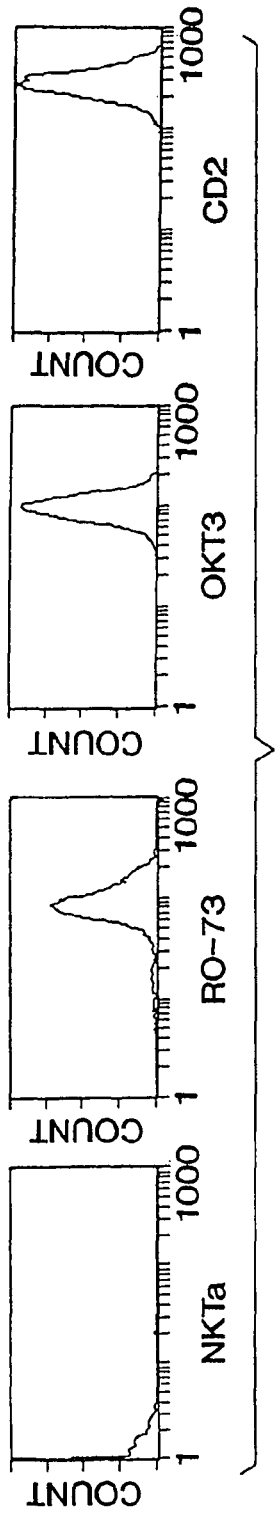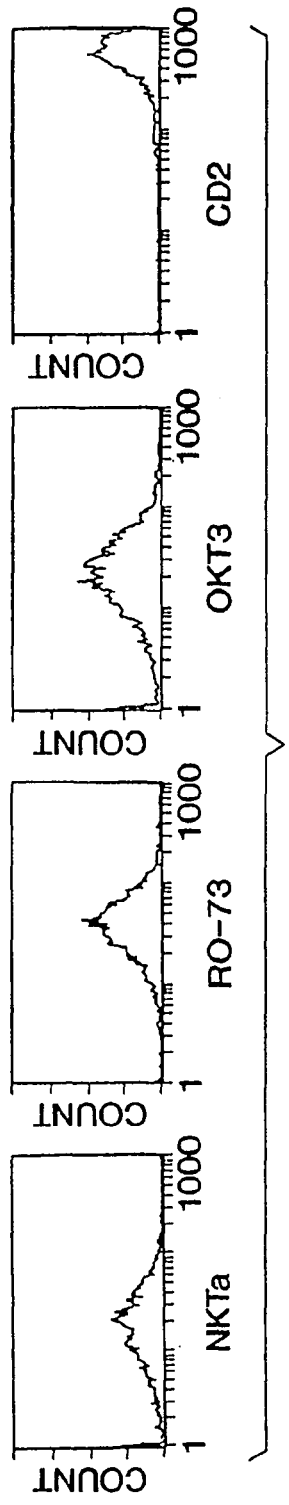

SEQUENCE LISTING

<160> NUMBER OF SEQ ID NOS: 109

<210> SEQ ID NO 1
<211> LENGTH: 240
<212> TYPE: DNA
<213> ORGANISM: Homo sapiens
<220> FEATURE:
<221> NAME/KEY: misc_feature
<223> OTHER INFORMATION: HBP25

<400> SEQUENCE: 1

```
ggacaggatg tagctctcag gtgtgatcca atttcgggtc atgtatccct ttattggtac      60
cgacaggccc tggggcaggg cccagagttt ctgacttact tcaattatga agcccaacaa     120
gacaaatcag ggctgcccaa tgatcggttc tctgcagaga ggcctgaggg atccatctcc     180
actctgacga tccagcgcac agagcagcgg gactcggcca tgtatcgctg tgccagcacc     240
```

<210> SEQ ID NO 2
<211> LENGTH: 387
<212> TYPE: DNA
<213> ORGANISM: Homo sapiens
<220> FEATURE:
<221> NAME/KEY: misc_feature
<223> OTHER INFORMATION: IGR b 02; V BETA w21

<400> SEQUENCE: 2

```
agtgaccctg atctggcaaa gcttccatcc tgccctgacc ctgccatggg taccaggctc      60
ctctgccggg tggccttctg tctcctggtg aagaactca tagaagctgg agtggttcag     120
tctcccagat ataagattat agagaaaaag cagcctgtgg cttttggtg caatcctatt     180
tctggccaca ataccctta ctggtaccgg cagaacttgg gacagggccc ggagcttctg     240
attcgatatg agaatgagga agcagtagac gattcacagt tgcctaagga tcgattttct     300
gcagagaggc tcaaaggagt agactccact ctcaagatcc agcctgcaga gcttggggac     360
tcggccgtgt atctctgtgc cagcagc                                         387
```

<210> SEQ ID NO 3
<211> LENGTH: 395
<212> TYPE: DNA
<213> ORGANISM: Homo sapiens
<220> FEATURE:
<221> NAME/KEY: misc_feature
<223> OTHER INFORMATION: IGR b 03; V BETA w22

<400> SEQUENCE: 3

```
acaggaccag atgcctgagc taggaaaggc ctcattcctg ctgtgatcct gccatggata      60
cctggctcgt atgctgggca attttttagtc tcttgaaagc aggactcaca gaacctgaag     120
tcacccagac tcccagccat caggtcacac agatgggaca ggaagtgatc ttgcgctgtg     180
tccccatctc taatcactta cttctatt ggtacagaca aatcttgggg cagaaagtcg     240
agtttctggt ttccttttat aataatgaaa tctcagagaa gtgtgaaata ttcgatgatc     300
aattctcagt tgaaaggcct gatggatcaa atttcactct gaagatccgg tccacaaagc     360
tggaggactc agccatgtac ttctgtgcca gcagt                                395
```

<210> SEQ ID NO 4
<211> LENGTH: 329
<212> TYPE: DNA
<213> ORGANISM: Homo sapiens
<220> FEATURE:
<221> NAME/KEY: misc_feature
<223> OTHER INFORMATION: IGR b 04; V BETA w23

<400> SEQUENCE: 4

```
agctcctctg ccatgtcatg ctttgtctcc tgggagcagg ttcagtggct gctggagtca    60
tccagtcccc aagacatctg atcaaagaaa agagggaaac agccactctg aaatgctatc   120
ctatccctag acacgacact gtctactggt accagcaggg tccaggtcag gaccccagt    180 tcctcatttc gttttatgaa aagatgcaga gcgataaagg aagcatccct gatcgattct   240
cagctcaaca gttcagtgac tatcattctg aactgaacat gagctccttg gagctggggg   300
actcagccct gtacttctgt gccagcagc                                     329
```

<210> SEQ ID NO 5
<211> LENGTH: 366
<212> TYPE: DNA
<213> ORGANISM: Homo sapiens
<220> FEATURE:
<221> NAME/KEY: misc_feature
<223> OTHER INFORMATION: IGR b 05; V BETA w24

<400> SEQUENCE: 5

```
attcctgtat ggggtggtat tcctgccatg ggtcctgggc ttctccactg gatggccctt    60
tgtctccttg gaacaggtca tggggatgcc atggtcatcc agaacccaag ataccaggtt   120
acccagtttg gaaagccagt gaccctgagt tgttctcaga ctttgaacca taacgtcatg   180
tactggtacc agcagaagtc aagtcaggcc ccaaagctgc tgttccacta ctatgacaaa   240
gattttaaca atgaagcaga caccctgat aacttccaat ccaggaggcc gaacacttct   300
ttctgctttc ttgacatccg ctcaccaggc ctggggacg cagccatgta cctgtgtgcc   360
accagc                                                              366
```

<210> SEQ ID NO 6
<211> LENGTH: 238
<212> TYPE: DNA
<213> ORGANISM: Homo sapiens
<220> FEATURE:
<221> NAME/KEY: misc_feature
<223> OTHER INFORMATION: IGR b 06;  V BETA 5

<400> SEQUENCE: 6

```
aggacagcaa gcgactctga gatgctctcc tatctctggg cacaccagtg tgtactggta    60
ccaacaggcc ctgggtctgg gcctccagct cctcctttgg tatgacgagg gtgaagagag   120
aaacagagga aacttccctc ctagattttc aggtcgccag ttccctaatt atagctctga   180
gctgaatgtg aacgccttgg agctgaggag ctcggccctg tatctctgtg ccagcagc     238
```

<210> SEQ ID NO 7
<211> LENGTH: 192
<212> TYPE: DNA
<213> ORGANISM: Homo sapiens
<220> FEATURE:
<221> NAME/KEY: misc_feature
<223> OTHER INFORMATION: IGR b 07;  V BETA 5

<400> SEQUENCE: 7

```
actgtgtcct ggtaccaaca ggccctgggt caggggcccc agtttatctt tcagtattat    60
agggaggaag agaatggcag aggaaactcc cctcctagat tctcaggtct ccagttccct   120
aattatagct ctgagctgaa tgtgaacgcc ttggagctgg acgactcggc cctgtatctc   180
tgtgccagca gc                                                       192
```

<210> SEQ ID NO 8
<211> LENGTH: 410
<212> TYPE: DNA
<213> ORGANISM: Homo sapiens
<220> FEATURE:
<221> NAME/KEY: misc_feature
<223> OTHER INFORMATION: IGR b 08; V BETA 5

<400> SEQUENCE: 8

```
gaactcactg ggttcttccc caggaggacc aagccctgaa tcaggtgcag tgctgcctgc      60
cccactgtgc catgggccct gggctcctct gctgggtgct gctttgtctc ctgggagcag     120
gcccagtgga cgctggagtc acccaaagtc ccacacacct gatcaaaacg agaggacagc     180
aagtgactct gagatgctct cctatctctg agcacaagag tgtgtcctgg taccaacagg     240
tcctgggtca ggggccccag tttatctttc agtattatga aaagaagag agaggaagag      300
gaaacttccc tgatcgattc tcagctcgcc agttccctaa ctatagctct gagctgaatg     360
tgaacgcctt gttgctgggg gactcggccc tgtatctctg tgccagcagc                410
```

<210> SEQ ID NO 9
<211> LENGTH: 380
<212> TYPE: DNA
<213> ORGANISM: Homo sapiens
<220> FEATURE:
<221> NAME/KEY: misc_feature
<223> OTHER INFORMATION: IGR b 09; V BETA 5

<400> SEQUENCE: 9

```
aagccctgaa tcagatgcag tgcttcctgt ccctctgtgc catgggcccc gggctcctct      60
gctgggcact gctttgtctc ctgggagcag gcttagtgga cgctggagtc acccaaagtc     120
ccacacacct gatcaaaacg agaggacagc aagtgactct gagatgctct cctaagtctg     180
ggcatgacac tgtgtcctgg taccaacagg ccctgggtca ggggcccag tttatctttc      240
agtattatga ggaggaagag agacagagag gcaacttccc tgatcgattc tcaggtcacc     300
agttccctaa ctatagctct gagctgaatg tgaacgcctt gttgctgggg gactcggccc     360
tctatctctg tgccagcagc                                                  380
```

<210> SEQ ID NO 10
<211> LENGTH: 351
<212> TYPE: DNA
<213> ORGANISM: Homo sapiens
<220> FEATURE:
<221> NAME/KEY: misc_feature
<223> OTHER INFORMATION: IGR b 11; V BETA 6

<400> SEQUENCE: 10

```
gaccctgcca tgggcaccag tctcctatgc tgggtggtcc tgggtttcct agggacagat      60
cacacaggtg ctggagtctc ccagtctccc aggtacaaag tcacaaagag gggacaggat     120
gtagctctca ggtgtgatcc aatctcgggt catgtatccc tttattggta ccgacaggcc     180
ctggggcagg gcccagagtt tctgacttac ttcaattatg aagcccaaca agacaaatca     240
gggctgccca tgatcggtt ctctgcagag aggcctgagg gatccatctc cactctgacg      300
atccagcgca cagagcagcg ggactcggcc atgtatcgct gtgccagcag c               351
```

<210> SEQ ID NO 11
<211> LENGTH: 238
<212> TYPE: DNA
<213> ORGANISM: Homo sapiens
<220> FEATURE:
<221> NAME/KEY: misc_feature
<223> OTHER INFORMATION: IGR b 12; V BETA 6

<400> SEQUENCE: 11

```
aaaggatgta gagctcaggt gtgatccaat ttcaggtcat actgcccttt actggtaccg      60
acagagcctg gggcagggcc tggagttttt aatttacttc caaggcaaca gtgcaccaga     120
caaatcaggg ctgcccaacg atcggttctt tgcagtcagg cctgagggat ccgtctctac     180
tctgaggatc cagcgcacag agcgggggga ctcagccgtg tatctctgtg ccagcagc      238
```

<210> SEQ ID NO 12
<211> LENGTH: 294
<212> TYPE: DNA
<213> ORGANISM: Homo sapiens
<220> FEATURE:
<221> NAME/KEY: misc_feature
<223> OTHER INFORMATION: IGR b 13; V BETA 12

<400> SEQUENCE: 12

```
tcaggacaca gggatgctga aatcacccag agcccaagac acaagatcac agagacagga      60
aggcaggtga ccttggcgtg tcaccagact tggaaccaca acaatatgtt ctggtatcga     120
caagacctgg gacatgggct gaggctgatc cattactcat atggtgttca agacactaac     180
aaaggagaag tctcagatgg ctacagtgtc tctagatcaa acacagagga cctcccctc     240 actctggagt ctgctgcctc ctcccagaca tctgtatatt tctgcgccag cagg          294
```

<210> SEQ ID NO 13
<211> LENGTH: 369
<212> TYPE: DNA
<213> ORGANISM: Homo sapiens
<220> FEATURE:
<221> NAME/KEY: misc_feature
<223> OTHER INFORMATION: IGR b 14; V BETA 13

<400> SEQUENCE: 13

```
agaagacccc tccatcctgt agcacctgcc atgagcatcg ggctcctgtg ctgtgtggcc      60 tttttctctcc tgtgggcaag tccagtgaat gctggtgtca ctcagacccc aaaattccag    120
gtcctgaaga caggacagag catgacactg cagtgtgccc aggatatgaa ccataactcc    180
atgtactggt atcgacaaga cccaggcatg ggactgaggc tgatttatta ctcagcttct    240
gagggtacca ctgacaaagg agaagtcccc aatggctaca atgtctccag attaaacaaa    300
cgggagttct cgctcaggct ggagtcggct gctccctccc agacatctgt gtacttctgt    360
gccagcacc                                                            369
```

<210> SEQ ID NO 14
<211> LENGTH: 356
<212> TYPE: DNA
<213> ORGANISM: Homo sapiens
<220> FEATURE:
<221> NAME/KEY: misc_feature
<223> OTHER INFORMATION: IGR b 15; V BETA 13

<400> SEQUENCE: 14

```
tgcttgtagc atctgccatg agaatcaggc tcctgtgctg tgtggccttt tctctcctgt      60
gggcaggtcc agtgattgct gggatcaccc aggcaccaac atctcagatc ctggcagcag    120
gacggcgcat gacactgaga tgtacccagg atatgagaca taatgccatg tactggtata    180
gacaagatct aggactgggg ctaaggctca tccattattc aaatactgca ggtaccactg    240
gcaaaggaga agtccctgat ggttatagtg tctccagagc aaaacagat gatttccccc     300 tcacgttggc gtctgctgta ccctctcaga catctgtgta cttctgtgcc agcagt         356
```

```
<210> SEQ ID NO 15
<211> LENGTH: 345
<212> TYPE: DNA
<213> ORGANISM: Homo sapiens
<220> FEATURE:
<221> NAME/KEY: misc_feature
<223> OTHER INFORMATION: IGR b 16; V BETA

<400> SEQUENCE: 15
aaggcccagc ccctttccat tggggctgca gcatcagctg tttccttctc tgcaggtcca      60
gtgaatgctg gtgtcactca gaccccaaaa ttccgcatcc tgaagatagg acagagcatg     120
acactgcagt gtgcccagga tatgaaccat aactacatgt actggtatcg acaagaccca     180
ggcatggggc tgaagctgat ttattattca gttggtgctg gtatcactga taaaggagaa     240
gtcccgaatg gctacaacgt ctccagatca accacagagg atttcccgct caggctggag     300
ttggctgctc cctcccagac atctgtgtac ttctgtgcca gcagt                     345

<210> SEQ ID NO 16
<211> LENGTH: 450
<212> TYPE: DNA
<213> ORGANISM: Homo sapiens
<220> FEATURE:
<221> NAME/KEY: misc_feature
<223> OTHER INFORMATION: IGR b 17;  V BETA 7

<400> SEQUENCE: 16
tggagcagtg acatcacagg aaaaaccacc aaccaaggcc aaggagacca gagcccagca      60
cctcacccag aggaccccag tcagaggccc catctcagac ccgaggctag catgggctgc     120
aggctgctct gctgtgcggt tctctgtctc ctgggagcgg tccccatgga acgggagtt     180 acgcagacac caagacacct ggtcatggga atgacaaata gaagtctttt gaaatgtgaa     240
caacatctgg ggcataacgc tatgtattgg tacaagcaaa gtgctaagaa gccactggag     300
ctcatgtttg tctacaactt taaagaacag actgaaaaca acagtgtgcc aagtcgcttc     360
tcacctgaat gccccaacag ctctcactta tgccttcacc tacacaccct gcagccagaa     420
gactcggccc tgtatctctg tgccagcacc                                      450

<210> SEQ ID NO 17
<211> LENGTH: 354
<212> TYPE: DNA
<213> ORGANISM: Homo sapiens
<220> FEATURE:
<221> NAME/KEY: misc_feature
<223> OTHER INFORMATION: IGR b 18; V BETA 7

<400> SEQUENCE: 17
agacccgagg ctagcatggg ctgcaggctg ctctgctctg cggttctctg tctcctggga      60
gcggtcccca tggaaacggg agttacgcag acaccaagac acctggtcat gggaatgaca     120
aataagaagt ctttgaaatg tgaacaacat ctgggtcata cgctatgta ttggtacaag     180 caaagtgcta agaagccact ggagctcatg tttgtctaca gtcttgaaga acggggtgaa     240
aacaacagtg tgccaagtcg cttctcacct gaatgcccca cagctctca cttatcccctt     300 cacctacaca ccctgcagcc agaagactcg gccctgtatc tctgcgccag cagc          354

<210> SEQ ID NO 18
<211> LENGTH: 368
<212> TYPE: DNA
<213> ORGANISM: Homo sapiens
<220> FEATURE:
<221> NAME/KEY: misc_feature
```

<223> OTHER INFORMATION: IGR b 19; V BETA 7

<400> SEQUENCE: 18

```
agaggcccca tctcagaccc gaggctagca tgggctgcag gctgctctgc tgtgcggttc    60
tctgtctcct gggagcagtt cccatagaca ctgaagttac ccagacacca aaacacctgg   120
tcatgggaat gacaaataag aagtctttga aatgtgaaca acatatgggg cacagggcta   180
tgtattggta caagcagaaa gctaagaagc caccggagct catgtttgtc tacagctatg   240
agaaactctc tataaatgaa agtgtgccaa gtcgcttctc acctgaatgc cccaacagct   300
ctctcttaaa ccttcaccta cacgccctgc agccagaaga ctcagccctg tatctctgcg   360
ccagcagc                                                            368
```

<210> SEQ ID NO 19
<211> LENGTH: 432
<212> TYPE: DNA
<213> ORGANISM: Homo sapiens
<220> FEATURE:
<221> NAME/KEY: misc_feature
<223> OTHER INFORMATION: IGR b 20; V BETA 9

<400> SEQUENCE: 19

```
acctctcaac ggcagtgaaa ccacagccta gtcctctcac cactgcagac cagaatcctg    60
ccctgggcct tgcctggtct gcctcactct gccatgggct gcaggctcct ctgctgtgtg   120
gtcttctgcc tcctccaagc aggtcccttg acacagctg tttcccagac tccaaaatac   180
ctggtcacac agatgggaaa cgacaagtcc attaaatgtg aacaaaatct gggccatgat   240
actatgtatt ggtataaaca ggactctaag aaatttctga agataatgtt tagctacaat   300
aataaggagc tcattataaa tgaaacagtt ccaaatcgct tctcacctaa atctccagac   360
aaagctcact taaatcttca catcaattcc ctggagcttg gtgactctgc tgtgtatttc   420
tgtgccagca gc                                                       432
```

<210> SEQ ID NO 20
<211> LENGTH: 24
<212> TYPE: DNA
<213> ORGANISM: Homo sapiens
<220> FEATURE:
<221> NAME/KEY: misc_feature
<223> OTHER INFORMATION: Primer A

<400> SEQUENCE: 20

```
tatctggagt cattgagggc gggc                                           24
```

<210> SEQ ID NO 21
<211> LENGTH: 35
<212> TYPE: DNA
<213> ORGANISM: Homo sapiens
<220> FEATURE:
<221> NAME/KEY: misc_feature
<223> OTHER INFORMATION: POLY C PRIMER

<400> SEQUENCE: 21

```
gcatgcgcgc ggccgcggag gccccccccc ccccc                               35
```

<210> SEQ ID NO 22
<211> LENGTH: 25
<212> TYPE: DNA
<213> ORGANISM: Homo sapiens
<220> FEATURE:
<221> NAME/KEY: misc_feature
<223> OTHER INFORMATION: PRIMER B

<400> SEQUENCE: 22
tgtggccagg catgccagtg tggcc           25

<210> SEQ ID NO 23
<211> LENGTH: 24
<212> TYPE: DNA
<213> ORGANISM: Homo sapiens
<220> FEATURE:
<221> NAME/KEY: misc_feature
<223> OTHER INFORMATION: PRIMER C

<400> SEQUENCE: 23
ggtgtgggag aattctgctt ctga           24

<210> SEQ ID NO 24
<211> LENGTH: 19
<212> TYPE: DNA
<213> ORGANISM: Homo sapiens
<220> FEATURE:
<221> NAME/KEY: misc_feature
<223> OTHER INFORMATION: OLIGONUCLEOTIDE D

<400> SEQUENCE: 24
tctgcttctg atggctcaa           19

<210> SEQ ID NO 25
<211> LENGTH: 24
<212> TYPE: DNA
<213> ORGANISM: Homo sapiens
<220> FEATURE:
<221> NAME/KEY: misc_feature
<222> LOCATION: (251)..()
<223> OTHER INFORMATION: TYPE V BETA 1, CLONE HBVT73

<400> SEQUENCE: 25
ccgcacaaca gttccctgac ttgc           24

<210> SEQ ID NO 26
<211> LENGTH: 24
<212> TYPE: DNA
<213> ORGANISM: Homo sapiens
<220> FEATURE:
<221> NAME/KEY: misc_feature
<222> LOCATION: (210)..()
<223> OTHER INFORMATION: TYPE V BETA 2, CLONE MOLT 4

<400> SEQUENCE: 26
ggccacatac gagcaaggcg tcga           24

<210> SEQ ID NO 27
<211> LENGTH: 24
<212> TYPE: DNA
<213> ORGANISM: Homo sapiens
<220> FEATURE:
<221> NAME/KEY: misc_feature
<222> LOCATION: (232)..()
<223> OTHER INFORMATION: TYPE V BETA 3, CLONE DT259, THE 11TH NUCLEOTIDE
      CORRESPONDS TO MISMATCHES INTRODUCED RELATIVE TO THE NATURAL
      SEQUENCE

<400> SEQUENCE: 27
cgcttctccc ggattctgga gtcc           24

<210> SEQ ID NO 28
<211> LENGTH: 24
<212> TYPE: DNA
<213> ORGANISM: Homo sapiens
<220> FEATURE:

```
<221> NAME/KEY: misc_feature
<222> LOCATION: (257)..()
<223> OTHER INFORMATION: TYPE V BETA 4, CLONE DT110

<400> SEQUENCE: 28
ttcccatcag ccgcccaaac ctaa                                            24

<210> SEQ ID NO 29
<211> LENGTH: 24
<212> TYPE: DNA
<213> ORGANISM: Homo sapiens
<220> FEATURE:
<221> NAME/KEY: misc_feature
<222> LOCATION: (199)..()
<223> OTHER INFORMATION: TYPE V BETA 5, CLONE VB12A1

<400> SEQUENCE: 29
agctctgagc tgaatgtgaa cgcc                                            24

<210> SEQ ID NO 30
<211> LENGTH: 24
<212> TYPE: DNA
<213> ORGANISM: Homo sapiens
<220> FEATURE:
<221> NAME/KEY: misc_feature
<222> LOCATION: (117)..()
<223> OTHER INFORMATION: THE V BETA 6, CLONE ATL12.2, THE 18TH
      NUCLEOTIDE CORRESPONDS TO MISMATCHES INTRODUCED RELATIVE TO THE
      NATURAL SEQUENCE

<400> SEQUENCE: 30
tctcaggtgt gatccaaatt cggg                                            24

<210> SEQ ID NO 31
<211> LENGTH: 24
<212> TYPE: DNA
<213> ORGANISM: Homo sapiens
<220> FEATURE:
<221> NAME/KEY: misc_feature
<222> LOCATION: (169)..()
<223> OTHER INFORMATION: TYPE V BETA 7, CLONE PL4.9

<400> SEQUENCE: 31
cctgaatgcc ccaacagctc tctc                                            24

<210> SEQ ID NO 32
<211> LENGTH: 24
<212> TYPE: DNA
<213> ORGANISM: Homo sapiens
<220> FEATURE:
<221> NAME/KEY: misc_feature
<222> LOCATION: (170)..()
<223> OTHER INFORMATION: TYPE V BETA 8, CLONE PH11

<400> SEQUENCE: 32
ccatgatgcg gggactggag ttgc                                            24

<210> SEQ ID NO 33
<211> LENGTH: 24
<212> TYPE: DNA
<213> ORGANISM: Homo sapiens
<220> FEATURE:
<221> NAME/KEY: misc_feature
<222> LOCATION: (201)..()
<223> OTHER INFORMATION: TYPE V BETA 9, CLONE PL2.6

<400> SEQUENCE: 33
ttccctggag cttggtgact ctgc                                            24
```

```
<210> SEQ ID NO 34
<211> LENGTH: 24
<212> TYPE: DNA
<213> ORGANISM: Homo sapiens
<220> FEATURE:
<221> NAME/KEY: misc_feature
<222> LOCATION: (299)..()
<223> OTHER INFORMATION: TYPE V BETA 10, CLONE ATL12-1

<400> SEQUENCE: 34
ccacggagtc agggacaca gcac                                              24

<210> SEQ ID NO 35
<211> LENGTH: 24
<212> TYPE: DNA
<213> ORGANISM: Homo sapiens
<220> FEATURE:
<221> NAME/KEY: misc_feature
<222> LOCATION: (297)..()
<223> OTHER INFORMATION: TYPE V BETA 11, CLONE PL3.12

<400> SEQUENCE: 35
tgccaggccc tcatacct ctca                                               24

<210> SEQ ID NO 36
<211> LENGTH: 24
<212> TYPE: DNA
<213> ORGANISM: Homo sapiens
<220> FEATURE:
<221> NAME/KEY: misc_feature
<222> LOCATION: (109)..()
<223> OTHER INFORMATION: TYPE V BETA 12, CLONE VBPH27, THE 14TH AND 23RD
      NUCLEOTIDES CORRESPOND TO MISMATCHES INTRODUCED RELATIVE TO THE
      NATURAL SEQUENCE

<400> SEQUENCE: 36
tgtcaccaga ctgggaacca ccac                                             24

<210> SEQ ID NO 37
<211> LENGTH: 24
<212> TYPE: DNA
<213> ORGANISM: Homo sapiens
<220> FEATURE:
<221> NAME/KEY: misc_feature
<222> LOCATION: (116)..()
<223> OTHER INFORMATION: TYPE V BETA 13, CLONE CEM-VB1, THE 7TH AND 12TH
      NUCLEOTIDES CORRESPOND TO MISMATCHES INTRODUCED RELATIVE TO THE
      NATURAL SEQUENCE

<400> SEQUENCE: 37
cactgcggtg tacccaggat atga                                             24

<210> SEQ ID NO 38
<211> LENGTH: 24
<212> TYPE: DNA
<213> ORGANISM: Homo sapiens
<220> FEATURE:
<221> NAME/KEY: misc_feature
<222> LOCATION: (175)..()
<223> OTHER INFORMATION: TYPE V BETA 14, CLONE VBPH21, THE 6TH AND 20TH
      NUCLEOTIDES CORRESPOND TO MISMATCHES INTRODUCED RELATIVE TO THE
      NATURAL SEQUENCE

<400> SEQUENCE: 38
gggctcggct taaggcagac ctac                                             24

<210> SEQ ID NO 39
<211> LENGTH: 24
<212> TYPE: DNA
```

```
<213> ORGANISM: Homo sapiens
<220> FEATURE:
<221> NAME/KEY: misc_feature
<222> LOCATION: (262)..()
<223> OTHER INFORMATION: TYPE V BETA 15, CLONE ALT2-1

<400> SEQUENCE: 39
caggcacagg ctaaattctc cctg                                          24

<210> SEQ ID NO 40
<211> LENGTH: 24
<212> TYPE: DNA
<213> ORGANISM: Homo sapiens
<220> FEATURE:
<221> NAME/KEY: misc_feature
<222> LOCATION: (192)..()
<223> OTHER INFORMATION: TYPE V BETA 16, CLONE HBP42

<400> SEQUENCE: 40
gcctgcagaa ctggaggatt ctgg                                          24

<210> SEQ ID NO 41
<211> LENGTH: 24
<212> TYPE: DNA
<213> ORGANISM: Homo sapiens
<220> FEATURE:
<221> NAME/KEY: misc_feature
<222> LOCATION: (254)..()
<223> OTHER INFORMATION: TYPE V BETA 17, CLONE VBPH29

<400> SEQUENCE: 41
ctgctgaatt tcccaaagag ggcc                                          24

<210> SEQ ID NO 42
<211> LENGTH: 24
<212> TYPE: DNA
<213> ORGANISM: Homo sapiens
<220> FEATURE:
<221> NAME/KEY: misc_feature
<223> OTHER INFORMATION: TYPE V BETA 18, CLONE HUT102

<400> SEQUENCE: 42
tgccccagaa tctctcagcc tcca                                          24

<210> SEQ ID NO 43
<211> LENGTH: 24
<212> TYPE: DNA
<213> ORGANISM: Homo sapiens
<220> FEATURE:
<221> NAME/KEY: misc_feature
<222> LOCATION: (279)..()
<223> OTHER INFORMATION: TYPE V BETA 19, CLONE HBVT02

<400> SEQUENCE: 43
tcctctcact gtgacatcgg ccca                                          24

<210> SEQ ID NO 44
<211> LENGTH: 24
<212> TYPE: DNA
<213> ORGANISM: Homo sapiens
<220> FEATURE:
<221> NAME/KEY: misc_feature
<222> LOCATION: (274)..()
<223> OTHER INFORMATION: TYPE V BETA 20, CLONE HBVT72

<400> SEQUENCE: 44
tctcaatgcc ccaagaacgc accc                                          24
```

```
<210> SEQ ID NO 45
<211> LENGTH: 24
<212> TYPE: DNA
<213> ORGANISM: Homo sapiens
<220> FEATURE:
<221> NAME/KEY: misc_feature
<222> LOCATION: (318)..()
<223> OTHER INFORMATION: TYPE V BETA w21, CLONE IGRb01I, THE 13TH AND
      20TH NUCLEOTIDES CORRESPOND TO MISMATCHES INTRODUCED RELATIVE TO
      THE NATURAL SEQUENCE

<400> SEQUENCE: 45
tccaacctgc aaggcttgac gact                                           24

<210> SEQ ID NO 46
<211> LENGTH: 24
<212> TYPE: DNA
<213> ORGANISM: Homo sapiens
<220> FEATURE:
<221> NAME/KEY: misc_feature
<222> LOCATION: (110)..()
<223> OTHER INFORMATION: TYPE V BETA w22, CLONE IGRb03

<400> SEQUENCE: 46
aagtgatctt gcgctgtgtc ccca                                           24

<210> SEQ ID NO 47
<211> LENGTH: 24
<212> TYPE: DNA
<213> ORGANISM: Homo sapiens
<220> FEATURE:
<221> NAME/KEY: misc_feature
<222> LOCATION: (155)..()
<223> OTHER INFORMATION: TYPE V BETA w23, CLONE IGRa04

<400> SEQUENCE: 47
gcagggtcca ggtcaggacc ccca                                           24

<210> SEQ ID NO 48
<211> LENGTH: 24
<212> TYPE: DNA
<213> ORGANISM: Homo sapiens
<220> FEATURE:
<221> NAME/KEY: misc_feature
<222> LOCATION: (95)..()
<223> OTHER INFORMATION: TYPE V BETA w24, CLONE IGRa05

<400> SEQUENCE: 48
cccagtttgg aaagccagtg accc                                           24

<210> SEQ ID NO 49
<211> LENGTH: 24
<212> TYPE: DNA
<213> ORGANISM: Homo sapiens
<220> FEATURE:
<221> NAME/KEY: misc_feature
<222> LOCATION: (71)..()
<223> OTHER INFORMATION: TYPE C BETA A

<400> SEQUENCE: 49
ggtgtgggag aattctgctt ctga                                           24

<210> SEQ ID NO 50
<211> LENGTH: 24
<212> TYPE: DNA
<213> ORGANISM: Homo sapiens
<220> FEATURE:
<221> NAME/KEY: misc_feature
<222> LOCATION: (135)..()
<223> OTHER INFORMATION: TYPE C BETA B
```

-continued

```
<400> SEQUENCE: 50
accagctcag ctccgcgggg tcgg                                              24

<210> SEQ ID NO 51
<211> LENGTH: 19
<212> TYPE: DNA
<213> ORGANISM: Homo sapiens
<220> FEATURE:
<221> NAME/KEY: misc_feature
<222> LOCATION: (58)..()
<223> OTHER INFORMATION: TYPE C BETA C

<400> SEQUENCE: 51
tctgcttctg atggctcaa                                                    19

<210> SEQ ID NO 52
<211> LENGTH: 24
<212> TYPE: DNA
<213> ORGANISM: Homo sapiens
<220> FEATURE:
<221> NAME/KEY: misc_feature
<222> LOCATION: (1161)..()
<223> OTHER INFORMATION: TYPE ACT 1, CLONE BETA-ACTIN

<400> SEQUENCE: 52
atttgcggtg gacgatggag gggc                                              24

<210> SEQ ID NO 53
<211> LENGTH: 24
<212> TYPE: DNA
<213> ORGANISM: Homo sapiens
<220> FEATURE:
<221> NAME/KEY: misc_feature
<222> LOCATION: (261)..()
<223> OTHER INFORMATION: TYPE ACT 2, CLONE BETA-ACTIN

<400> SEQUENCE: 53
ggcatcgtca ccaactggga cgac                                              24

<210> SEQ ID NO 54
<211> LENGTH: 19
<212> TYPE: DNA
<213> ORGANISM: Homo sapiens
<220> FEATURE:
<221> NAME/KEY: misc_feature
<222> LOCATION: (642)..()
<223> OTHER INFORMATION: TYPE ACT 3, CLONE BETA ACTIN

<400> SEQUENCE: 54
accaccacgg cggagcggg                                                    19

<210> SEQ ID NO 55
<211> LENGTH: 24
<212> TYPE: DNA
<213> ORGANISM: Homo sapiens
<220> FEATURE:
<221> NAME/KEY: misc_feature
<222> LOCATION: (201)..()
<223> OTHER INFORMATION: TYPE C ALPHA E

<400> SEQUENCE: 55
gttgctccag gccgcggcac tgtt                                              24

<210> SEQ ID NO 56
<211> LENGTH: 24
<212> TYPE: DNA
<213> ORGANISM: Homo sapiens
```

```
<220> FEATURE:
<221> NAME/KEY: misc_feature
<222> LOCATION: (12)..()
<223> OTHER INFORMATION: TYPE C ALPHA J

<400> SEQUENCE: 56
ccctgaccct gccgtgtacc agct                                              24

<210> SEQ ID NO 57
<211> LENGTH: 19
<212> TYPE: DNA
<213> ORGANISM: Homo sapiens
<220> FEATURE:
<221> NAME/KEY: misc_feature
<222> LOCATION: (57)..()
<223> OTHER INFORMATION: TYPE C ALPHA C

<400> SEQUENCE: 57
gtcactggat ttagagtct                                                    19

<210> SEQ ID NO 58
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 1, THE 6TH AND 23RD NUCLEOTIDES
      CORRESPOND TO MISMATCHES INTRODUCED RELATIVE TO THE NATURAL
      SEQUENCE

<400> SEQUENCE: 58
ggcattaacg gttttgaggc tgga                                              24

<210> SEQ ID NO 59
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 2, THE 24TH NUCLEOTIDE CORRESPONDS
      TO A MISMATCH INTRODUCED RELATIVE TO THE NATURAL SEQUENCE

<400> SEQUENCE: 59
cagtgttcca gagggagcca ttgc                                              24

<210> SEQ ID NO 60
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 3

<400> SEQUENCE: 60
ccgggcagca gacactgctt ctta                                              24

<210> SEQ ID NO 61
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 4

<400> SEQUENCE: 61
ttggtatcga cagcttccct ccca                                              24

<210> SEQ ID NO 62
```

```
<211> LENGTH: 24
<212> TYPE: DNA
<213> ORGANISM: Homo sapiens
<220> FEATURE:
<221> NAME/KEY: misc_feature
<223> OTHER INFORMATION: type v alpha 5

<400> SEQUENCE: 62
cggccaccct gacctgcaac tata                                               24

<210> SEQ ID NO 63
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 6

<400> SEQUENCE: 63
tccgccaacc ttgtcatctc cgct                                               24

<210> SEQ ID NO 64
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 7, THE 9TH AND 15TH NUCLEOTIDES
      CORRESPOND TO MISMATCHES INTRODUCED RELATIVE TO THE NATURAL
      SEQUENCE

<400> SEQUENCE: 64
gcaacatgct ggcggagcac ccac                                               24

<210> SEQ ID NO 65
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 8

<400> SEQUENCE: 65
cattcgttca aatgtgggca aaag                                               24

<210> SEQ ID NO 66
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 9, THE 22ND NUCLEOTIDE CORRESPONDS
      TO A MISMATCH INTRODUCED RELATIVE TO THE NATURAL SEQUENCE

<400> SEQUENCE: 66
ccagtactcc agacaacgcc tgca                                               24

<210> SEQ ID NO 67
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 10

<400> SEQUENCE: 67
cactgcggcc cagcctggtg atac                                               24
```

```
<210> SEQ ID NO 68
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 11

<400> SEQUENCE: 68
cgctgctcat cctccaggtg cggg                                              24

<210> SEQ ID NO 69
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 12

<400> SEQUENCE: 69
tcgtcggaac tcttttgatg agca                                              24

<210> SEQ ID NO 70
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 13

<400> SEQUENCE: 70
ttcatcaaaa cccttgggga cagc                                              24

<210> SEQ ID NO 71
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 14

<400> SEQUENCE: 71
cccagcaggc agatgattct cgtt                                              24

<210> SEQ ID NO 72
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 15, THE 12TH NUCLEOTIDE
      CORRESPONDS TO A MISMATCH INTRODUCED RELATIVE TO THE NATURAL
      SEQUENCE

<400> SEQUENCE: 72
ttgcagacac cgagactggg gact                                              24

<210> SEQ ID NO 73
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 16

<400> SEQUENCE: 73
tcaacgttgc tgaagggaat cctc                                              24
```

```
<210> SEQ ID NO 74
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 17, THE 12TH NUCLEOTIDE
      CORRESPONDS TO A MISMATCH INTRODUCED RELATIVE TO THE NATURAL
      SEQUENCE

<400> SEQUENCE: 74
tgggaaaggc cgtgcattat tgat                                          24

<210> SEQ ID NO 75
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 18

<400> SEQUENCE: 75
cagcaccaat ttcacctgca gctt                                          24

<210> SEQ ID NO 76
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 19

<400> SEQUENCE: 76
acactggctg caacagcatc cagg                                          24

<210> SEQ ID NO 77
<211> LENGTH: 24
<212> TYPE: DNA
<213> ORGANISM: Homo sapiens
<220> FEATURE:
<221> NAME/KEY: misc_feature
<223> OTHER INFORMATION: type v alpha 20

<400> SEQUENCE: 77
tccctgttta tccctgccga caga                                          24

<210> SEQ ID NO 78
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 21

<400> SEQUENCE: 78
agcaaaattc accatccctg agcg                                          24

<210> SEQ ID NO 79
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha 22

<400> SEQUENCE: 79
cctgaaagcc acgaaggctg atga                                          24
```

-continued

```
<210> SEQ ID NO 80
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha w23

<400> SEQUENCE: 80
tgcctcgctg gataaatcat cagg                                              24

<210> SEQ ID NO 81
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha w24, THE 21ST NUCLEOTIDE
      CORRESPONDS TO A MISMATCH INTRODUCED RELATIVE TO THE NATURAL
      SEQUENCE

<400> SEQUENCE: 81
ctggatgcag acacaaagca gagc                                              24

<210> SEQ ID NO 82
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha w25, THE 7TH AND 17TH NUCLEOTIDES
      CORRESPOND TO MISMATCHES INTRODUCED RELATIVE TO THE NATURAL
      SEQUENCE

<400> SEQUENCE: 82
tggctacggt acaagccgga ccct                                              24

<210> SEQ ID NO 83
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha w26, THE 4TH AND 20TH NUCLEOTIDES
      CORRESPOND TO MISMATCHES INTRODUCED RELATIVE TO THE NATURAL
      SEQUENCE

<400> SEQUENCE: 83
agcgcagcca tgcaggcatg tacc                                              24

<210> SEQ ID NO 84
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha w27

<400> SEQUENCE: 84
aagcccgtct cagcaccctc caca                                              24

<210> SEQ ID NO 85
<211> LENGTH: 24
<212> TYPE: DNA
<213> ORGANISM: Homo sapiens
<220> FEATURE:
<221> NAME/KEY: misc_feature
<223> OTHER INFORMATION: type v alpha w28, THE 8TH AND 15TH NUCLEOTIDES
      CORRESPOND TO MISMATCHES INTRODUCED RELATIVE TO THE NATURAL
      SEQUENCE
```

```
<400> SEQUENCE: 85
tggttgtgca cgagcgagac actg                                              24

<210> SEQ ID NO 86
<211> LENGTH: 24
<212> TYPE: DNA
<213> ORGANISM: Homo sapiens
<220> FEATURE:
<221> NAME/KEY: misc_feature
<223> OTHER INFORMATION: TYPE V Alpha w29

<400> SEQUENCE: 86
gaagggtgga gaacagatgc gtcg                                              24

<210> SEQ ID NO 87
<211> LENGTH: 24
<212> TYPE: DNA
<213> ORGANISM: Homo sapiens
<220> FEATURE:
<221> NAME/KEY: misc_feature
<223> OTHER INFORMATION: TYPE C Alpha A

<400> SEQUENCE: 87
atacacatca gaattcttac tttg                                              24

<210> SEQ ID NO 88
<211> LENGTH: 24
<212> TYPE: DNA
<213> ORGANISM: Homo sapiens
<220> FEATURE:
<221> NAME/KEY: misc_feature
<223> OTHER INFORMATION: TYPE C Alpha B

<400> SEQUENCE: 88
gttgctccag gccgcggcac tgtt                                              24

<210> SEQ ID NO 89
<211> LENGTH: 264
<212> TYPE: DNA
<213> ORGANISM: Homo sapiens
<220> FEATURE:
<221> NAME/KEY: misc_feature
<223> OTHER INFORMATION: VB12A1

<400> SEQUENCE: 89
gcagcactgc acctgatcaa aacgagagga cagcacgtga ctctgagatg ctctcctatc        60
tctgggcaca agagtgtgtc ctggtaccaa caggtcctgg gtcagggggcc ccagtttatc      120 tttcagtatt atgagaaaga agagagagga agaggaaact tccctgatcg attctcagct      180
cgccagttcc ctaactatag ctctgagctg aatgtgaacg ccttgttgct gggggactcg      240
gccctgtatc tctgtgccag cagc                                             264

<210> SEQ ID NO 90
<211> LENGTH: 339
<212> TYPE: DNA
<213> ORGANISM: Homo sapiens
<220> FEATURE:
<221> NAME/KEY: misc_feature
<223> OTHER INFORMATION: HBP51

<400> SEQUENCE: 90
atgggctcca ggctgctctg ttgggtgctg ctttgtctcc tgggagcagg cccagtaaag        60
gctggagtca ctcaaactcc aagatatctg atcaaaacga gaggacagca agtgacactg      120
```

```
agctgctccc ctatctctgg gcataggagt gtatcctggt accaacagac cccaggacag    180
ggccttcagt tcctctttga atacttcagt gagacacaga gaaacaaagg aaacttccct    240
ggtcgattct cagggcgcca gttctctaac tctcgctctg agatgaatgt gagcaccttg    300
gagctggggg actcggccct ttatctttgc gccagcagc                            339
```

```
<210> SEQ ID NO 91
<211> LENGTH: 331
<212> TYPE: DNA
<213> ORGANISM: Homo sapiens
<220> FEATURE:
<221> NAME/KEY: misc_feature
<223> OTHER INFORMATION: PH24

<400> SEQUENCE: 91
```

```
caggcggcac tgttgggtgc tgctttgtct cctaggagca ggcccggtaa gggctggggt    60
cactcaaact ccaagacatc tgatcaaaac gagaggacag caagtgacac tgggctgctc    120
ccctatctct gggcatagga gtgtatcctg gtaccaacag accctaggac agggccttca    180
gttcctcttt gaatacttca gtgagacaca gagaaacaaa ggaaacttcc ttggtcgatt    240
ctcagggcgc cagttctcta actctcgctc tgagatgaat gtgagcacct tggagctggg    300
ggactcggcc ctttatcttt gcgccagcgc t                                    331
```

```
<210> SEQ ID NO 92
<211> LENGTH: 235
<212> TYPE: DNA
<213> ORGANISM: Homo sapiens
<220> FEATURE:
<221> NAME/KEY: misc_feature
<223> OTHER INFORMATION: PL2.5

<400> SEQUENCE: 92
```

```
acagcaagtg actctgagat gctctcctaa gtctgggcat gacactgtgt cctggtacca    60
acaggccctg ggtcaggggc cccagtttat ctttcagtat tatgaggagg aagagagaca    120
gagaggcaac ttccctgatc gattctcagg tcaccagttc cctaactata gctctgagct    180
gaatgtgaac gccttgttgc tgggggactc ggccctctat ctctgtgcca gcagc         235
```

```
<210> SEQ ID NO 93
<211> LENGTH: 303
<212> TYPE: DNA
<213> ORGANISM: Homo sapiens
<220> FEATURE:
<221> NAME/KEY: misc_feature
<223> OTHER INFORMATION: HT11

<400> SEQUENCE: 93
```

```
ttgggggcag atcacgcaga tactggagtc tcccagaacc ccagacacaa gatcacaaag    60
aggggacaga atgtaacttt caggtgtgat ccaatttctg aacacaaccg ccttttattgg   120 taccgacaga ccctggggca gggcccagag tttctgactt acttccagaa tgaagctcaa    180
ctagaaaaat caaggctgct cagtgatcgg ttctctgcag agaggcctaa gggatctttc    240
tccaccttgg agatccagcg cacagagcag ggggactcgg ccatgtatct ctgtgccagc    300
agc                                                                   303
```

```
<210> SEQ ID NO 94
<211> LENGTH: 342
<212> TYPE: DNA
<213> ORGANISM: Homo sapiens
<220> FEATURE:
<221> NAME/KEY: misc_feature
```

<223> OTHER INFORMATION: PH22

<400> SEQUENCE: 94

| | | |
|---|---|---|
| atggggacca gcctcctctg ctggatggcc ctctgtctcc tggggggcaga tcaggagata | 60 |
| tctggagtct cccacaaccc cagacacaag atcacaaaga ggggacagaa tgtaactttc | 120 |
| aggtgtgatc caatttctga acacaaccgc ctttattggt accgacagaa ccctgggcag | 180 |
| ggcccagagt ttctgactta cttccagaat gaagctcaac tggaaaaatc agggctgctc | 240 |
| agtgatcgga tctctgcaga gaggcctaag ggatctttct ccaccttgga gatccagcgc | 300 |
| acagagcagg gggactcggc catgtatctc tgtgccagca gc | 342 |

<210> SEQ ID NO 95
<211> LENGTH: 372
<212> TYPE: DNA
<213> ORGANISM: Homo sapiens
<220> FEATURE:
<221> NAME/KEY: misc_feature
<223> OTHER INFORMATION: CDS1

<400> SEQUENCE: 95

| | | |
|---|---|---|
| gtaaagctcc catcctgccc tgaccctgcc atgggcacca gcctcctctg ctggatggcc | 60 |
| ctgtgtctcc tggggggcaga tcacgcagat actggagtct cccagaaccc cagacacaac | 120 |
| atcacaaaga ggggacagaa tgtaactttc aggtgtgatc caatttctga acacaaccgc | 180 |
| ctttattggt accgacagac cctggggcag ggcccagagt ttctgactta cttccagaat | 240 |
| gaagctcaac tagaaaaatc aaggctgctc agtgatcgga tctctgcaga gaggcctaag | 300 |
| ggatctttct ccaccttgga gatccagcgc acagagcagg gggactcggc catgtatctc | 360 |
| tgtgccagca gc | 372 |

<210> SEQ ID NO 96
<211> LENGTH: 318
<212> TYPE: DNA
<213> ORGANISM: Homo sapiens
<220> FEATURE:
<221> NAME/KEY: misc_feature
<223> OTHER INFORMATION: HT116

<400> SEQUENCE: 96

| | | |
|---|---|---|
| atggccctct gtctcttggg ggcagatcac gcagatactg gagtctccca gaaccccaga | 60 |
| cacaagatca caaagagggg acagaatgta actttcaggt gtgatccaat ttctgaacac | 120 |
| aaccgccttt attggtaccg acagaccctg ggcagggcc cagagtttct gacttacttc | 180 |
| cagaatgaag ctcaactaga aaaatcaagg ctgctcagtg atcggttctc tgcagagagg | 240 |
| cctaagggat ctctctccac cttggagatc cagcgcacag agcaggggga ctcggccatg | 300 |
| tatctctgtg ccagcacc | 318 |

<210> SEQ ID NO 97
<211> LENGTH: 362
<212> TYPE: DNA
<213> ORGANISM: Homo sapiens
<220> FEATURE:
<221> NAME/KEY: misc_feature
<223> OTHER INFORMATION: AT122

<400> SEQUENCE: 97

| | | |
|---|---|---|
| catcctggcc tgaccctgcc atgggcacca ggctcctctg ctgggtggtc gcggtttcc | 60 |
| tagggacaga tcacacaggt gctggagtct cccagtcccc taggtacaaa gtcgcaaaga | 120 |
| gaggacagga tgtagctctc agtgtgtgatc caatttcggg tcatgtatcc cttttttggt | 180 |

```
accaacaggc cctggggcag gggccagagt ttctgactta tttccagaat gaagctcaac    240
tagacaaatc ggggctgccc agtgatcgct tctttgcaga aaggcctgag ggatccgtct    300
ccactctgaa gatccagcgc acacagcagg aggactccgc cgtgtatctc tgtgccagca    360
gc                                                                  362

<210> SEQ ID NO 98
<211> LENGTH: 343
<212> TYPE: DNA
<213> ORGANISM: Homo sapiens
<220> FEATURE:
<221> NAME/KEY: misc_feature
<223> OTHER INFORMATION: PH16

<400> SEQUENCE: 98
atgggcacca ggctcctctt ctgggtggcc ttctgtctcc tgggggcaga tcacacagga     60
gctggagtct cccagtcccc cagtaacaag gtcacagaga agggaaagga tgtagagctc    120
aggtgtgatc caatttcagg tcatactgcc ctttactggt accgacagag cctggggcag    180
ggcctggagt tttttaattta cttccaaggc aacagtgcac ctagacaaat cagggctgcc    240
cagtgatcgc ttctctgcag agaggactgg gggatccgtc tccactctga cgatccagcg    300
cacacagcag gaggactcgg ccgtgtatct ctgtgccagc agc                      343

<210> SEQ ID NO 99
<211> LENGTH: 330
<212> TYPE: DNA
<213> ORGANISM: Homo sapiens
<220> FEATURE:
<221> NAME/KEY: misc_feature
<223> OTHER INFORMATION: GLPA

<400> SEQUENCE: 99
caccaggctc ctcttctggg tggccttctg tctcctgggg gcatatcaca caggagctgg     60
agtctcccag tccccagta acaaggtcac agagaaggga aggatgtag agctcaggtg    120 tgatccaatt tcaggtcata ctgccctttta ctggtaccga cagaggctgg ggcagggcct    180 ggagtttttta atttacttcc aaggcaacag tgcaccagac aaatcagggc tgcccagtga    240
tcgcttctct gcagagagga ctggggaatc cgtctccact ctgacgatcc agcgcacaca    300
gcaggaggac tcggccgtgt atctctgtgc                                    330

<210> SEQ ID NO 100
<211> LENGTH: 303
<212> TYPE: DNA
<213> ORGANISM: Homo sapiens
<220> FEATURE:
<221> NAME/KEY: misc_feature
<223> OTHER INFORMATION: HT45

<400> SEQUENCE: 100
gtctccacag atcacacagg agctggagtt cccagtccc ccagtaacaa ggtcacagag     60
aagggaaagg atgtagagct caggtgtgat ccaatttcag gtcatactgc cctttactgg    120
taccgacaga gcctggggca gggcctggag tttttaattt acttccaagg caacagtgca    180
ccagacaaat cagggctgcc cagtgatcgc ttctctgcag agaggactgg gggatccgtc    240
tccactctga cgatccagcg cacacagcag gaggactcgg ccgtgtatct ctgtgccagc    300
agc                                                                 303

<210> SEQ ID NO 101
```

<211> LENGTH: 342
<212> TYPE: DNA
<213> ORGANISM: Homo sapiens
<220> FEATURE:
<221> NAME/KEY: misc_feature
<223> OTHER INFORMATION: HBP50

<400> SEQUENCE: 101

| | | | | | |
|---|---|---|---|---|---|
| atgggcacca | ggctcctctg | ctgggcagcc | ctgtgcctcc | tgggggcaga | tcacacaggt | 60
| gctggagtct | cccagacccc | cagtaacaag | gtcacagaga | agggaaaata | tgtagagctc | 120
| aggtgtgatc | caatttcagg | tcatactgcc | ctttactggt | accgacaaag | cctggggcag | 180
| ggcccagagt | ttctaattta | cttccaaggc | acggtgcgg | cagatgactc | agggctgccc | 240
| aacgatcggt | tctttgcagt | caggcctgag | ggatccgtct | ctactctgaa | gatccagcgc | 300
| acagagcggg | gggactcagc | cgtgtatctc | tgtgccagca | gc | | 342

<210> SEQ ID NO 102
<211> LENGTH: 231
<212> TYPE: DNA
<213> ORGANISM: Homo sapiens
<220> FEATURE:
<221> NAME/KEY: misc_feature
<223> OTHER INFORMATION: HBMLT

<400> SEQUENCE: 102

| | | | | | |
|---|---|---|---|---|---|
| tgggagctca | ggtgtgatcc | aatttcaggt | catactgccc | tttactggta | ccgacaaagc | 60
| ctggggcagg | gcccagagct | tctaatttac | ttccaaggca | cgggtgcggc | agatgactca | 120
| gggctgccca | acgatcggtt | ctttgcagtc | aggcctgagg | gatccgtctc | tactctgaag | 180
| atccagcgca | cagagcgggg | ggactcagcc | gtgtatctct | gtgccagcag | c | 231

<210> SEQ ID NO 103
<211> LENGTH: 324
<212> TYPE: DNA
<213> ORGANISM: Homo sapiens
<220> FEATURE:
<221> NAME/KEY: misc_feature
<223> OTHER INFORMATION: PH27

<400> SEQUENCE: 103

| | | | | | |
|---|---|---|---|---|---|
| caacttgtgc | cctttgtctc | ctgtggacag | gacacatgga | tggatgctgg | aatcacccag | 60
| agcccaagac | acaaggtcac | agagacagga | acaccagtga | ctctgagatg | tcaccagact | 120
| gagaaccacc | gctatatgta | ctggtatcga | caagacccgg | ggcatgggct | gaggctgatc | 180
| cattactcat | atggtgttaa | agatactgac | aaaggagaag | tctcagatgg | ctatagtgtc | 240
| tctagatcaa | agacagagga | tttcctcctc | actctggagt | ccgctaccag | ctcccagaca | 300
| tctgtgtact | tctgtgccat | cagc | | | | 324

<210> SEQ ID NO 104
<211> LENGTH: 237
<212> TYPE: DNA
<213> ORGANISM: Homo sapiens
<220> FEATURE:
<221> NAME/KEY: misc_feature
<223> OTHER INFORMATION: PL4.2

<400> SEQUENCE: 104

| | | | | | |
|---|---|---|---|---|---|
| ggaacaccag | tgactctgag | atgtcaccag | actgagaacc | accgctacat | gtactggtat | 60
| cgacaagacc | cggggcatgg | gctgaggcta | atccattact | catatggtgt | taaagatact | 120
| gacaaaggag | aagtctcaga | tggctatagt | gtctctagat | caaagacaga | ggatttcctc | 180

```
ctcactctgg agtcgctacc agctcccgag acatctgtgt acttctgtgc cactaga        237
```

<210> SEQ ID NO 105
<211> LENGTH: 339
<212> TYPE: DNA
<213> ORGANISM: Homo sapiens
<220> FEATURE:
<221> NAME/KEY: misc_feature
<223> OTHER INFORMATION: HBVP34

<400> SEQUENCE: 105

```
atgagcatcg gcctcctgtg ctgtgcagcc ttgtctctcc tgtgggcagg tccagtgaat         60
gctggtgtca ctcagacccc aaaattccag gtcctgaaga caggacagag catgacactg        120
cagtgtgccc aggatatgaa ccatgaatac atgtcctggt atcgacaaga cccaggcatg        180
gggctgaggc tgattcatta ctcagttggt gctggtatca ctgaccaagg agaagtcccc        240
aatggctaca atgtctccag atcaaccaca gaggatttcc cgctcaggct gctgtcggct        300
gctccctccc agacatctgt gtacttctgt gccagcagt                               339
```

<210> SEQ ID NO 106
<211> LENGTH: 352
<212> TYPE: DNA
<213> ORGANISM: Homo sapiens
<220> FEATURE:
<221> NAME/KEY: misc_feature
<223> OTHER INFORMATION: CEM

<400> SEQUENCE: 106

```
ctcgagttcc tgccatgagc ctcgggctcc tgtgctgtgg ggccttttct ctcctgtggg         60
caggtccagt gaatgctggt gtcactcaga ccccaaaatt ccgggtcctg aagacaggac        120
agagcatgac actgctgtgt gcccaggata tgaaccatga atacatgtac tggtatcgac        180
aagacccagg catgggctga ggctgattca ttactcagtt ggtgagggta caactgccaa        240
aggagaggtc cctgatggct acaatgtctc cagattaaaa aaacagaatt tcctgctggg        300
gttggagtcg gctgctccct cccaaacatc tgtgtacttc tgtgccagca gc               352
```

<210> SEQ ID NO 107
<211> LENGTH: 108
<212> TYPE: DNA
<213> ORGANISM: Homo sapiens
<220> FEATURE:
<221> NAME/KEY: misc_feature
<223> OTHER INFORMATION: PL4.19

<400> SEQUENCE: 107

```
attcgctcca gtggcttctc acctgaatgc cccaacagct ctcacttatt ccttcaccta         60
cacaccctgc agccagaaga ctcggccctg tatctctgcg ccagcagc                    108
```

<210> SEQ ID NO 108
<211> LENGTH: 255
<212> TYPE: DNA
<213> ORGANISM: Homo sapiens
<220> FEATURE:
<221> NAME/KEY: misc_feature
<223> OTHER INFORMATION: PL4.9

<400> SEQUENCE: 108

```
cacctggtca tgggaatgac aaataagaag tctttgaaat gtgaacaaca tatggggcac         60
agggcaatgt attggtacaa gcagaaagct aagaagccac cggagctcat gtttgtctac        120
agctatgaga aactctctat aaatgaaagt gtgccaagtc gcttctcacc tgaatgcccc        180
```

```
aacagctctc tcttaaacct tcacctacac gccctgcagc cagaagactc agccctgtat      240
ctctgcgcca gcagc                                                      255

<210> SEQ ID NO 109
<211> LENGTH: 246
<212> TYPE: DNA
<213> ORGANISM: Homo sapiens
<220> FEATURE:
<221> NAME/KEY: misc_feature
<223> OTHER INFORMATION: PL2.6

<400> SEQUENCE: 109
acagagttgg gaaacgacaa gtccattaaa tgtgaacaaa atctgggcca tgatactatg       60
tattggtata aacaggactc taagaaattt ctgaagataa tgtttagcta caataataag      120
gagctcatta taaatgaaac agttccaaat cgcttctcac ctaaatctcc agacaaagct      180
cacttaaatc ttcacatcaa ttccctggag cttggtgact ctgctgtgta tttctgtgcc      240
agcagc                                                                246
```

NUCLEOTIDE SEQUENCE CODING FOR VARIABLE REGIONS OF β CHAINS OF HUMAN T LYMPHOCYTE RECEPTORS, CORRESPONDING PEPTIDE SEGMENTS AND THE DIAGNOSTIC AND THERAPEUTIC USES

The present invention relates to new nucleotide sequences coding for variable regions of β chain T-cell receptors, corresponding peptide segments and the diagnostic and therapeutic uses.

It is known that the receptors recognizing antigens at the surface of mature T lymphocytes (hereafter designated T-cell receptors) possess a structure having a certain similarity with those of immunoglobulins. Therefore, they contain heterodimeric structures containing α and β glycoprotein chains or γ and δ glycoprotein chains (see Meuer et al. (1), Moingeon et al. (2), Brenner et al. (3), Bank et al. (4)).

The directory of T-cell receptors must be able to address the immense diversity of antigenic determinants. This is obtained by genetic recombination of different discontinuous segments of genes which code for the different structural regions of T-cell receptors. Thus, the genes contain V segments (variable segments), optionally D segments (diversity segments), J segments (junction segments) and C segments (constant segments). During the differentiation of T-cells, specific genes are created by recombination of V, D and J segments for the and β and δ loci and V and J segments for the α and β loci. These specific combinations as well as the pairing of two chains create the combinational diversity. This diversity is highly amplified by two supplementary mechanisms, namely the imprecise recombination of V-D-J or V-J segments and the addition of nucleotides corresponding to the N region (Davis et al. (5)).

A certain number of genetic V segments are already known. These segments have been grouped into subfamilies as a function of the similarity of sequences. By definition, the segments which have more than 75% similarity in the nucleotide sequence have been considered as members of the same subfamily (Crews et al. (6)). At present, about 60 distinct Vβ genetic segments are known (Wilson et al. (7), Robinson (8), Leider et al. (9), Reynolds (10), Li et al. (11)) which have been classified into 20 subfamilies, 7 of which have only one member (see Wilson et al. already quoted).

Furthermore, monoclonal antibodies directed against specific segments of the variable parts of T-cell receptors, in particular the β and δ chains, were recently described in WO 90/06758. These monoclonal antibodies are useful not only as diagnostic tools but also as therapeutic tools, for example, vis-a-vis rheumatoid arthritis.

The use of synthetic peptides corresponding to the variable regions of the α or β chains in the treatment of auto-immune diseases was also described (27 and 28).

It is also known that variations exist from one individual to another in the expression of different variable segments of the T-cell receptor in man (27 and 28).

The present invention aims to enrich the directory of genetic segments coding for the variable regions of the β chains of T-cell receptors by providing new V β genetic segments belonging to new subfamilies or belonging to subfamilies of which at least one member is already known.

Therefore a subject of the present invention is nucleotide sequences coding for the variable regions of β chains of human T lymphocyte receptors, corresponding to cDNAs containing nucleotide sequences chosen from any one of the V β segments corresponding to one of the sequences SEQ ID No. 2 to 19, and the sequences which differ from them by one or more nucleotides.

More particularly a subject of the present invention is: sequences coding for the variable regions of β chains of human T lymphocyte receptors, corresponding to cDNAs containing nucleotide sequences chosen from any one of the V β segments corresponding to one of the sequences SEQ ID No. 2 to 5, and the sequences which differ from them by one or more nucleotides.

The expression "and sequences which differ from them by one or more nucleotides", encompasses alleles which differ by up to 8 nucleotides, but more often differ by 1 or 2 nucleotides, or which can differ by the deletion or addition of one or two codons.

Also a more particular subject of the invention is:
nucleotide sequences coding for the variable regions of β chains of human T lymphocyte receptors, corresponding to cDNAs corresponding to all or part of the nucleotide sequences chosen from any one of the Vβ segments corresponding to one of the sequences SEQ ID No. 2 to 5, and the sequences which differ from them by one or two nucleotides, nucleotide sequences coding for the variable regions of the β chains of human T lymphocyte receptors, corresponding to cDNAs corresponding to one of the nucleotide sequences chosen from any one of the Vβ segments corresponding to one of the sequences SEQ ID No. 6 to 15, the sequences which differ from them by one or two nucleotides and fragments of the latter, in particular, the fragments of sequences which correspond to all or part of the nucleotide sequences chosen from any one of the V segments corresponding to one of the sequences:

1 to 155 of SEQ ID No. 8
1 to 125 of SEQ ID No. 9
1 to 111 of SEQ ID No. 10 and the sequences which differ from them by one or two nucleotides, nucleotide sequences coding for the variable regions of the β chains of human T lymphocyte receptors, corresponding to cDNAs corresponding to all or part of the nucleotide sequences chosen from any one of the Vβ segments corresponding to one of the sequences:

1 to 195 of SEQ ID No. 16
1 to 99 of SEQ ID No. 17
1 to 113 of SEQ ID No. 18
1 to 186 of SEQ ID No. 19, and the sequences which differ from them by one or two nucleotides.

By the expression "nucleotide sequences corresponding to cDNAs corresponding to all or part of the nucleotide sequences" is also designated the complete sequences as well as fragments of these sequences, including short fragments which can be used as probes (generally containing at least 10 nucleotides) or as primers (generally containing at least 15 nucleotides). In a general fashion, the present invention encompasses the group of new oligonucleotides which are fragments of Vβ sequences according to the invention.

As for the sequences which differ by one or two nucleotides, they correspond to variations which are observed experimentally at the time of determination of the nucleotide sequence of several cDNAs.

Also a subject of the present invention is the peptides coded by the nucleotide sequences according to the invention as well as the alleles and the derivatives of the latter which have the same function.

In a general fashion, the present invention encompasses the peptides constituted by or composed of a peptide sequence coded by the nucleotide sequences according to the invention as well as fragments of these peptides. It also encompasses the peptides which differ from the latter by one or more amino acids and which have the same function. These peptides can correspond to modifications such as those known with muteins or to allelic variations. In fact it has been shown in particular that certain genetic segments coding for the variable regions of chains of T receptors in man were subjected to a phenomenon of genetic polymorphism called allelic variation (29). The present invention encompasses the peptides resulting from this phenomenon.

The nucleotide sequences according to the invention have been obtained according to the following stages:
- isolation of the RNAs of peripheral lymphocytes of an individual;
- obtaining the complementary DNA using reverse transcriptase and a primer A which is specific to the Cβ region (SEQ ID No. 20);
- genetic amplification (by Anchored Polymerase Chain Reaction or A-PCR) using a DNA polymerase, a poly C primer (SEQ ID No. 21) and a primer B which is specific to the Cβ region (SEQ ID No. 22);
- a new amplification by A-PCR using DNA polymerase and a primer C which is specific to the Cβ region (SEQ ID No. 23);
- insertion in a plasmid vector;
- transformation of a bacterial host with the recombinant vector;
- screening of recombinant bacterial colonies with a labelled oligonucleotide D which is specific to Cβ (SEQ ID No. 24);
- extraction of plasmids from positive colonies;
- and sequencing of DNA fragments containing the Cβ region.

The present invention can be reproduced, in particular, by bispecific genetic amplification (polymerase chain reaction or PCR) by starting with the peripheral lymphocytes which express the mRNAs including the variable or junctional β segments corresponding to sequences ID No. 2 to 19 of the invention or alternatively by applying this PCR technique to genomic DNA of any somatic cell of an individual taken at random. The invention can also be reproduced by preparing the above genetic sequences by the chemical synthesis of oligonucleotides.

The peptides according to the invention can be obtained by standard peptide synthesis. They can also be obtained by the application of known genetic engineering techniques including the insertion of a DNA sequence coding for a peptide according to the invention into an expression vector such as a plasmid and the transformation of cells with this expression vector.

Therefore a subject of the present invention is also plasmids and expression vectors containing a DNA sequence coding for a peptide according to the invention as well as the hosts transformed with this vector.

Also a subject of the present invention is antibodies, and, in particular, monoclonal antibodies, directed against an antigenic determinant belonging to or composed of a peptide according to the invention.

The monoclonal antibodies may be obtained by any of the techniques which allow the production of antibody molecules from cell line culture. These techniques include different techniques using hybridomas.

The antibody production may be obtained in animals by the immunization of the animals by injection with the peptides or fragments according to the invention, whether they be natural, recombinant or synthetic, optionally after coupling to an immunogen such as tetanus anatoxin, or also by injection of human T lymphocytes expressing the corresponding sequences at their surface, including recombinant cells transfected with the corresponding coding sequences.

Also a subject of the present invention is hybridomas producing monoclonal antibodies directed against the polypeptides according to the invention.

The present invention also encompasses the fragments and the derivatives of monoclonal antibodies according to the invention which are reactive with defined variable regions of T-cell receptors. These fragments are, in particular, the $F(ab')_2$ fragments which can be obtained by the enzymatic cleavage of antibody molecules with pepsin, the Fab' fragments which can be obtained by reduction of the disulphide bridges of $F(ab')_2$ fragments and the Fab fragments which can be obtained by the enzymatic cleavage of antibody molecules with papain in-the presence of a reducing agent. The fragments can also be obtained by genetic engineering.

The monoclonal antibody derivatives are for example antibodies or fragments of these antibodies to which labellers such as a radio-isotope are attached. The monoclonal antibody derivatives are also antibodies or fragments of these antibodies to which therapeutically active molecules are attached, in particular, cytotoxic compounds.

The products of the invention have several uses in the field of diagnostics and in the field of therapeutics.

1—Uses in the Field of Diagnostics

The oligonucleotides contained in the nucleotide sequences according to the invention can be used to constitute detection probes (generally at least 10 nucleotides) which are capable of hybridizing with a variable region of a β chain or primers for the amplification of DNA (generally containing at least 15 nucleotides and preferably at least 17 nucleotides) which are capable of being linked to a sequence to be amplified.

Thus the oligonucleotides can be used in the diagnosis of immune disorders by detecting the presence of nucleic acid sequences which are homologues of a gene coding for the variable regions of β chains of T-cell receptors in the mRNA of a sample from a patient. Different methods can be used to establish a connection between the expression of T-cell genes and an illness. These methods include:
 a—the production and analysis of cDNA expression libraries obtained from T-cells connected with the illness to determine the frequency of dominant genes;
 b—Southern blot analysis of samples of genomic DNA to determine whether genetic polymorphisms or rearrangements of the genes coding for the T-cell receptors exist;
 c—the analysis of samples by obtaining cDNA, amplification by PCR and hybridization with labelled probes;
 d—the hybridization in situ of T-cells without culture of T-cells beforehand.

The primers can be used in PCR reactions in a method such as that defined in c.

The monoclonal antibodies, the fragments or the derivatives of these antibodies according to the invention can be used to study T-type immune responses, for example in the field of the auto-immune diseases of cancerology, of allergies, of transplants and of infectious diseases. In particular, the directory of different variable β segments of the T receptor can be studied, whether it be blood or tissue T-cells. In a general fashion the techniques used can be in vitro or in vivo methods.

With in vitro methods, the samples used can be samples of body fluids or tissue samples. The techniques used can include in particular flow cytofluorimetry to analyse blood T lymphocytes or labelling with immunoperoxidase on an anatomopathological section to study the lymphocytes infiltrating the tissues.

With in vivo methods, the antibodies, their fragments or their derivatives are administered by the usual routes, for example by intravenous route, and the immunospecific linkages are detected. This can be obtained for example in the case where an antibody is used which is labelled with a radio-isotope.

2—Uses in the Therapeutic Field

The oligonucleotides contained in the nucleotide sequences according to the invention can be used in therapeutics as anti sense oligonucleotides. In fact it is known that it is possible in vitro to inhibit the expression of a transcript gene in human lymphocytes by incubating these lymphocytes with an anti sense oligonucleotide specific to the gene in question (30). These anti sense oligonucleotides generally contain at least 10 and, preferably, at least 16 nucleotides. These anti sense oligonucleotides can be in particular the inverted and complemented sequences corresponding to 20 nucleotides upstream from the initiation site of the translation (ATG). The significance of the use in vitro of anti sense oligonucleotides specific to a Vβ genetic segment is to abolish (or strongly diminish) the expression of a T receptor containing this Vβ segment and thus to obtain a phenomenon of clonal deletion at the level of the specific reactivity of T lymphocytes. The anti sense oligonucleotides can not only be used in vitro on human T lymphocytes which are then reinjected, but also in vivo by local or systemic injection preferably after modification to increase the stability in vivo and the penetration into the lymphocytes of these oligonucleotides.

The monoclonal antibodies according to the invention can be used to modulate the immune system. It is in this way that the antibodies can be administered to block the interaction of the effector T-cells with their specific antigen. Anti T receptor antibodies linked for example to a cytotoxic molecule or a radio-isotope can also be administered so as to obtain a clonal deletion, thanks to the specific fixation on a β chain of a T-cell receptor. The monoclonal antibodies according to the invention can be used in therapeutics at low mitogenic concentrations so as to activate, in a specific fashion, certain sub-assemblies of T-cells or can be used at much higher concentrations to fix them to the receptors concerned and thus label these sub-assemblies with a view to their elimination by the reticulo-endothelial system. An important criterion in the treatment of an illness is the ability to modulate the sub-assemblies of T-cells linked with an illness. The exact nature of this therapeutic modulation, namely blocking or suppressing a particular sub-assembly of T-cells or on the contrary stimulating and activating a particular sub-assembly, will depend on the illness in question and the specific sub-assembly of T-cells concerned.

This type of treatment has an advantage over current treatments using antibodies such as the treatment with anti CD3 antibodies in patients having had a kidney transplant and having a rejection problem, given that thanks to the invention there will be no modulation of the totality of the T-cell population but only of the sub-assembly of T-cells expressing the β sub-family specific to the T-cell receptors.

Moreover, as the response of T-cells is often oligoclonal, it is generally convenient to use "cocktails" of several antibodies in therapeutics.

In addition anti Vβ antibodies can be used to select T lymphocytes in vitro, for example by passing through a column containing spheres carrying the antibody. This separation of certain T lymphocytes can be used with a view to culturing these lymphocytes before reinjection into the patient.

Moreover, all or part of the peptide sequences according to the invention can be used in therapeutics, that is to say the peptide sequences coded by the nucleotide sequences according to the invention or fragments of these sequences (generally containing at least 8 to 10 amino acids). These sequences or fragments, administered to humans or animals, can act as a decoy, that is to say they fix themselves on the epitope carried by the harmful antigen and stop the reaction of normal T-cells with the antigen, preventing in this way the development of an illness which is aggressive towards the self determinants. They can also be used as immunogens in the manufacture of vaccines (optionally after conjugation with protein carriers).

The invention will be described in greater detail hereafter by referring to the annexed figures in which:

FIGS. 1 to 6 show in a line both known Vβ sequences and partial sequences of new sequences according to the invention (SEQ ID No. 6 to 19), marked IGRa 08 to IGRa 20 belonging to known Vβ sub-families. In these figures, the numbering of nucleotides starts at the ATG initiation codon (which is underlined). The dots indicate identical nucleotides. The sequences which are assumed to be the leader sequences have a line over them.

FIG. 7 shows the Southern blot analyses of the genomic DNA treated with a restriction enzyme using probes specific to Vβ sub-families. The restriction enzymes used are EcoRI (column R), Hind III (column H) and Bam I (column B). On this figure the triangles mark the position of DNA fragments hybridizing in a specific fashion with Cβ.

The reactivity-control for NKTa or $OKT_3$ antibodies is given for each type of cell respectively.

The number of cells counted (linear scale) is given as a function of the intensity of fluorescence (logarithmic scale).

Figure 9A:
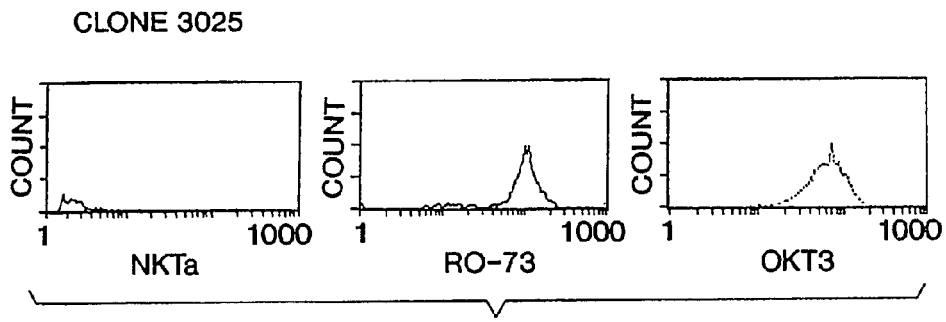
FIG. 9 represents the analysis by cytofluorimetry of the reactivity of the monoclonal antibody RO-73 vis-a-vis the immunizing clone 3025 (9A), clone 12410 (9B) and circulating lymphocytes (9C) respectively.
Figure 9B:
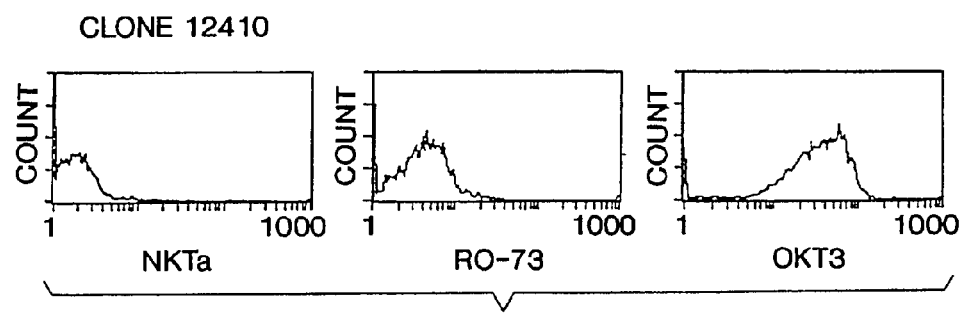
Figure 9C:
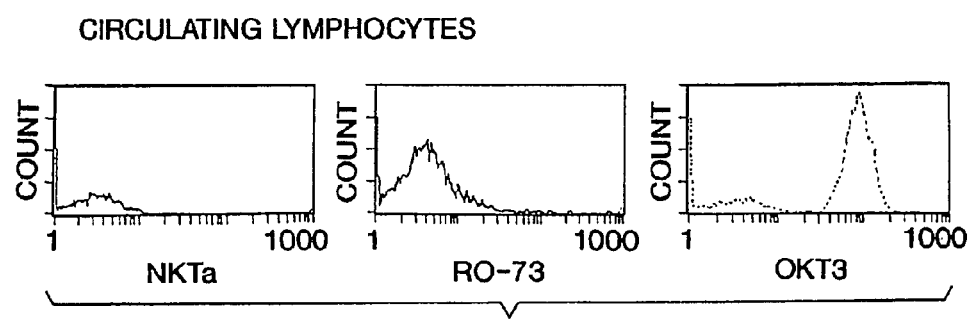
Figure 10A:
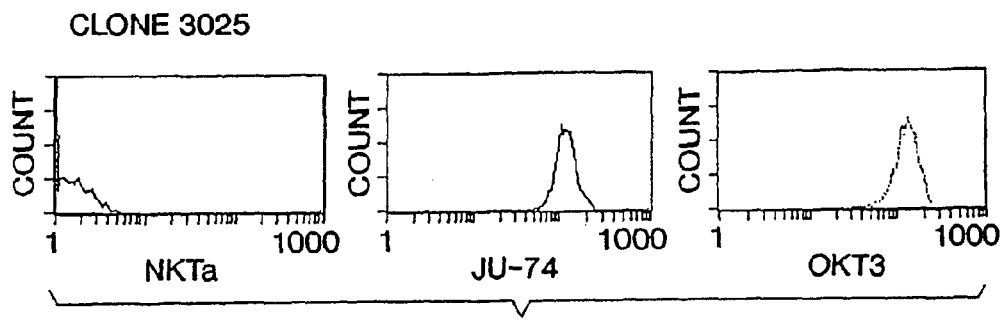
Figure 10B:
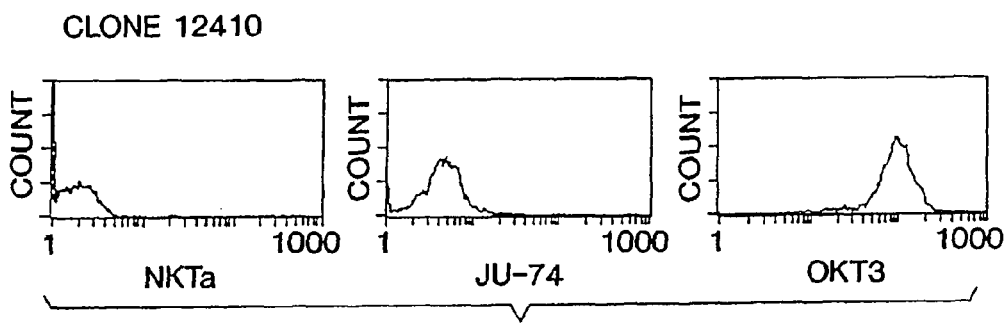
Figure 10C:
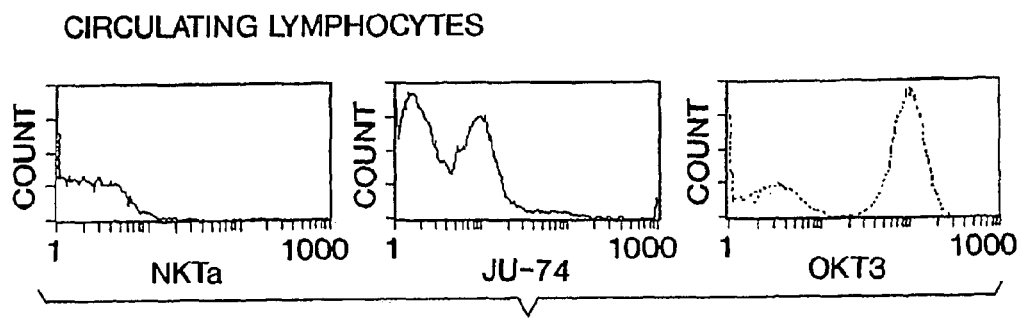

FIG. 10 represents the analysis by cytofluorimetry of the reactivity of the monoclonal antibody JU-74 (FIGS. 10A, 10B, 10C: same conditions as for FIGS. 9A, 9B, 9C).

FIG. 11 represents the analysis by cytofluorimetry of the comodulation with the CD3 molecule of the TCR structure of clone 3025 recognized by the monoclonal antibody RO-73 respectively in the absence (FIG. 11A) or in the presence of anti-CD3 antibodies (FIG. 11B).

The comodulation-control is given with the monoclonal antibodies NKTa, OKT3 and anti-CD2 respectively.

Figure 12A:
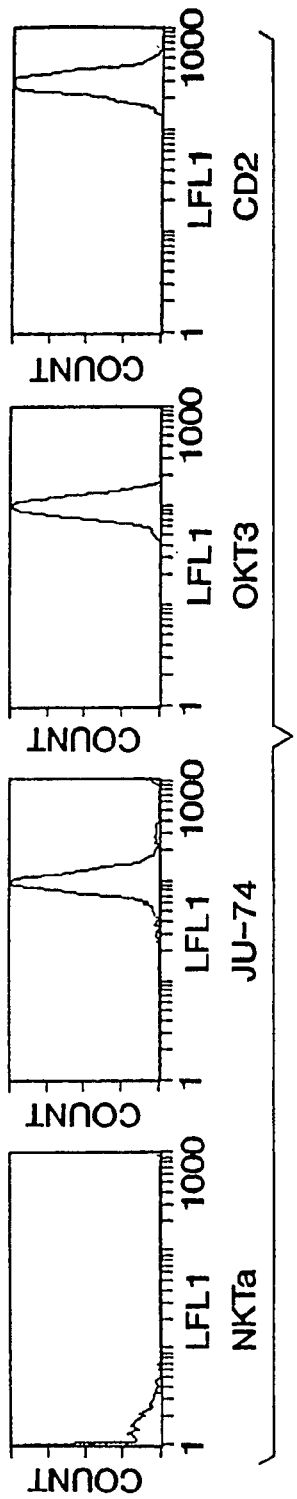
Figure 12B:
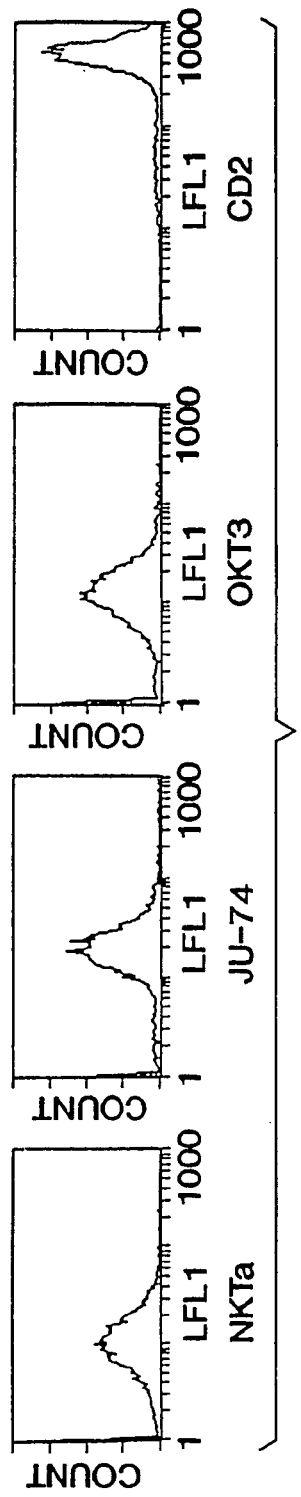

FIG. 12 represents the analysis by cytofluorimetry of the comodulation with the CD3 molecule of the TCR structure of clone 3025 recognized by the monoclonal antibody JU-73, respectively in the absence (FIG. 12A) or in the presence of anti-CD3 antibody (FIG. 12B).

Figure 13A:
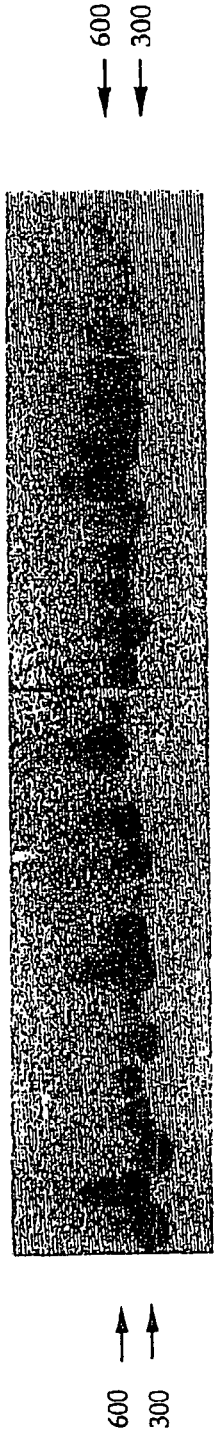
Figure 13B:
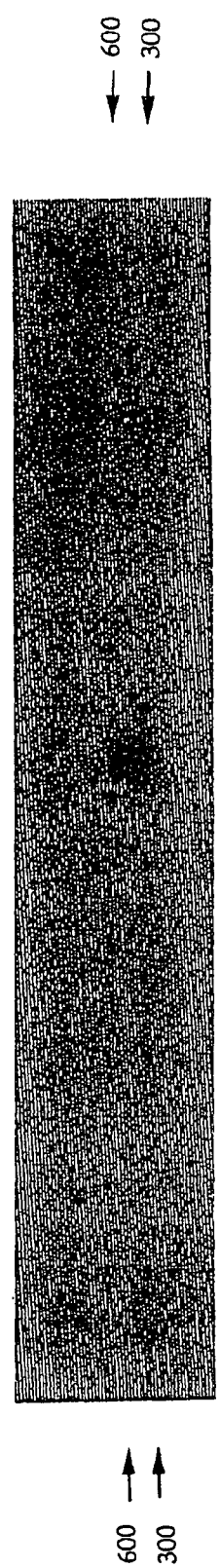

FIG. 13 represents the detection by autoradiography of amplified transcripts of TCR α chains (FIG. 13A) and β chains (FIG. 13B) expressed by the RO-73+ cells.

I—OBTAINING THE cDNA AND AMPLIFICATION BY PCR

The peripheral lymphocytes of an individual are used as the DNA source. The total RNA was prepared according to the method using guanidinium isothiocyanate and caesium chloride (Chirgwin (12)) or according to a one-stage method by extraction with guanidinium isothiocyanate, phenol and chloroform (Chomcyznski (13)).

The first cDNA strand was synthesized in a final volume of 50 microliters at a temperature of 42° C. for 1 hour using 5 micrograms of total RNA, reverse transcriptase and a primer A which is specific to the Cβ region constituted by the sequence 5'-TATCTGGAGTCATTGAGGGCGGGC (SEQ ID No. 20). This material was then purified by extraction with phenol/chloroform and precipitation with ammonium acetate. After selecting a 0.45/1 kb fraction on agarose gel, the addition of a dG end is carried out on the RNA/cDNA hetero complex in a $CoCl_2$ addition buffer with 14 units of terminal deoxynucleotidyl transferase (TdT) for 30 minutes at 37° C. The reaction was stopped by maintenance at 70° C. for 10 minutes. 1N NaOH (⅓ volume) was added and the sample was incubated at 50° C. for 1 hour to hydrolyze the RNA, then neutralized with Tris HCl 2M pH 8 and 1N HCl. After extraction with a phenol/chloroform mixture the first cDNA strand at end G was precipitated with ethanol and subjected to an amplification using the PCR technique (Polymerase Chain Reaction described by Saiki et al. (14)) in a final volume of 100 microliters containing 50 mM of KCl, 10 mM of Tris-Cl pH 8.3, 1.5 mM of $MgCl_2$, 0.1% (weight/volume) of gelatine, 200 micromoles of dNTP, 2.5 units of Taq polymerase and 100 picomoles of two primers. The two primers used are, on the one hand a poly-C primer (5'-GCATGCGCGCGGC-CGCGGAGG-14C) (SEQ ID No. 21) described by Loh et al. (15) as well as a primer B specific to the Cβ region (5'-TGTGGCCAGGCATGCCAGTGTGGCC) (SEQ ID No. 22).

25 amplification cycles are carried out followed by a final 15 minute elongation period at 72° C. Each cycle includes a denaturation stage at 92° C. for 1 minute, a hybridization stage at 55° C. for 2 minutes and an elongation period at 72° C. for 4 minutes. The amplified products are then precipitated with ethanol, resuspended in 30 mM of sodium acetate pH 5, 50 mM NaCl, 1 mM $ZnCl_2$, glycerol 5% by volume and (¹/₁₀) of this material is purified as a function of size on a 1% low melting point agarose gel.

A second amplification phase is then carried out directly on approximately 10% of the band containing the agarose following the same conditions as previously, except that the primer 5'-GGTGTGGGAGAATTCTGCTTC-TGA (SEQ ID No. 23) is used as primer C which is specific to the Cβ region. The reaction mixture is then precipitated with ethanol and resuspended in 60 μl of $H_2O$.

II—CLONING AND SEQUENCING OF cDNAs

⅓ of the product of the second amplification is digested with Sac II, separated on 1% agarose gel and purified by absorption on glass beads. The material is inserted in the Bluescript SK⁺ vector (Stratagene, La Jolla, U.S.A.) and the recombinants obtained are used to transform the XL1-blue strains of E. Coli (Stratagene). After sedimentation in the presence of x-gal and IPTG, a test is carried out on the white colonies using a "dot blot" technique and a third oligonucleotide specific to the Cβ region (5'-TCTGCTTCTGATGGCT-CAA) (SEQ ID No. 24) labelled with $^{32}P$ is used as a probe. The plasmid DNA of positive colonies is extracted and sequencing takes place under the two strands by the process of termination of the dideoxy chain (Sanger et al. (16)) with Sequenase 2.0 (United States Biochemicals, Cleveland, U.S.A.) following the supplier's recommendations.

The sequences obtained were compared with published Vβ sequences using the method developed by Lipman and Pearson (17). The presumed start codons were identified by searching for the presence of the Kozak consensus sequence for the initiation sites of translations in the eukaryotic cells (Kozak (18)). The presence of hydrophobic leader sequences of the N-terminal side was detected by analysis of the hydrophobicity according to the method described by Kyte (19).

III—SOUTHERN BLOT ANALYSIS

The DNA was extracted from the human erythroleukaemic cell line K562 and digested with one of the following restriction enzymes: Eco RI, BamH I or Hind III. The DNA (15 micrograms) was subjected to electrophoresis on 0.7% agarose and transferred onto Nylon membranes as described by Triebel et al. (20). The hybridizations were carried out at 65° C. with 6×SSC, 0.5% of SDS, 5×Denhardt's and 100 micrograms of denatured salmon sperm DNA for 16 hours. The membranes were washed at 65° C. with 2×SSC, 0.2% of SDS.

As Vβ specific probes, are used the probes obtained by amplification of V-J-C cDNA using as a primer the poly-C primer and the C primer. The probes were purified on 1% agarose gel. DNA probes labelled with $32_P$ were prepared from fragments purified on agarose by the Feinberg method (21).

IV—RESULTS

By using the A-PCR method, 350 cDNA which hybridize with the Cβ clone were cloned, then sequenced. Among these, 226 cDNA correspond to the V-J-Cβ variable regions only.

The Vβ sequences of the invention are shown in the list of sequences under SEQ ID No. 2 to 19. The sequences SEQ ID No. 3 to 5 correspond to three new sub-families while the sequences SEQ ID No. 2 and 6 to 19 correspond to new members of Vβ sub-families or to extensions of known Vβ segments.

Vβ w21 Sub-Family (SEQ ID No. 2)

This sub-family has been identified by the clone IGR b02 (SEQ ID No. 2).

This sequence shows for the coding part a similarity of about 85% with the sequence HSTCRB23 (Wilson et al. (41)).

Vβw22 Sub-Family (SEQ ID No. 3)

The segment SEQ ID No. 3 has been defined as a consensus sequence from 23 distinct clones of cDNA. A C instead of a T is observed in position 322 and an A instead of a G is observed in position 350.

Vβw23 Sub-Family (SEQ ID No. 4)

The segment ID No. 4 has been defined as a consensus sequence from 4 distinct clones. A G instead of an A is observed in position 154 and an A instead of a G is observed in position 160. It shows a similarity of 75.7% with the sequence VB12A1 (Leiden already quoted) but shows a similarity of less than 75% with the other members of the Vβ5 sub-family (represented in FIG. 1). Therefore it is not part of the V 5 sub-family.

Vβw24 Subfamily (SEQ ID No. 5)

The segment SEQ ID No. 5 has been defined from 2 distinct clones of cDNA.

Figure 7:
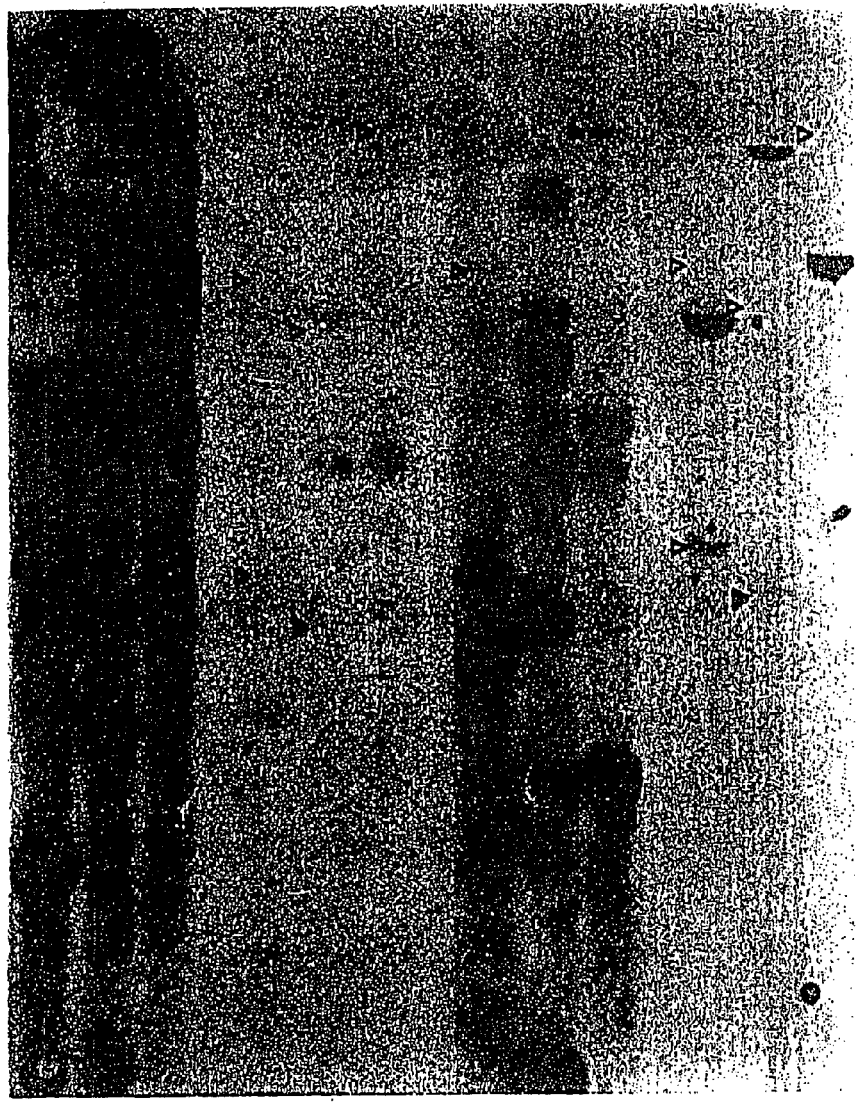

The Southern blot analyses of germinal line DNA subjected to digestion by endonucleases, using V-J-Cβ probes containing Vβ fragments corresponding to the Vβw21 to Vβw24 sub-families were carried out in "low stringency" hybridization conditions to identify the number of Vβ genetic segments belonging to each family and to characterize the DNA restriction fragments carrying these Vβ genetic segments. The representative results are shown in FIG. 7.

These analyses are compatible with the presence in the K 562 erythroleucemic cells of at least three genetic segments for the Vβw21 sub-family, two for the Vβw23 sub-family and one for the Vβw22 and Vβw24 sub-families.

The sizes of the germinal DNA restriction fragments are as follows:

Vβw21: EcoR I 1.7-, 3- and 6.5 kb, Hind III 2.5-, 7.2-, 11.7-, 14- and 18 kb, BamH I 5.5-, 16.5- and 23 kb;

Vβw22: EcoR I 2.8 kb, Hind III 8.8 kb, BamH I 5.3 kb;

Vβw23: EcoR I 3.2- and 4.4 kb, Hind III 7.4-, 15.5- and 16.5 kb, BamH I 2.5- and 5.7 kb;

Vβw24: EcoR I 8 kb, Hind III 20 kb and 7.3 kb, BamH I 11- and 22 kb.

Vβ5 Sub-Family (FIG. 1)

SEQ ID No. 6 and 7 (IGR b06 and IGR b07)

These sequences show a similarity of 79 to 86% and 76 to 70% respectively with the 4 previously known segments VB12A1 (Leiden already quoted), HBP51 (Kimura (23)), PH24 (Tillinghast already quoted) and PL25 (Concannon (24)) and represent new members.

SEQ ID No. 8 and 9 (IGR b08 and IGR b09)

These sequences correspond to extensions of the 5' side of VB12A1 and PL25 clones respectively. For SEQ ID No. 8 two nucleotide substitutions are observed relative to VB12A1.

Figure 2:
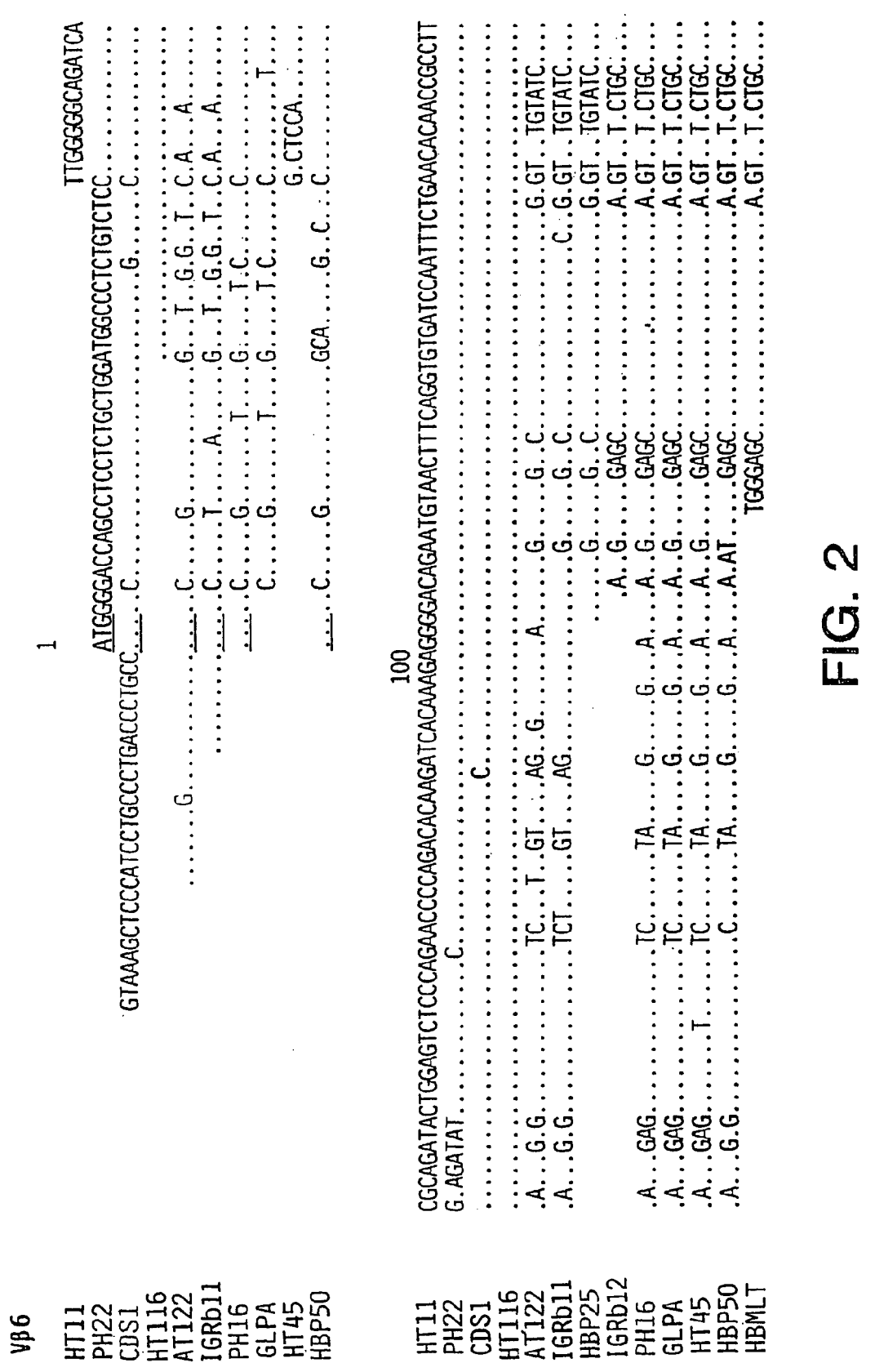
Figure 2:
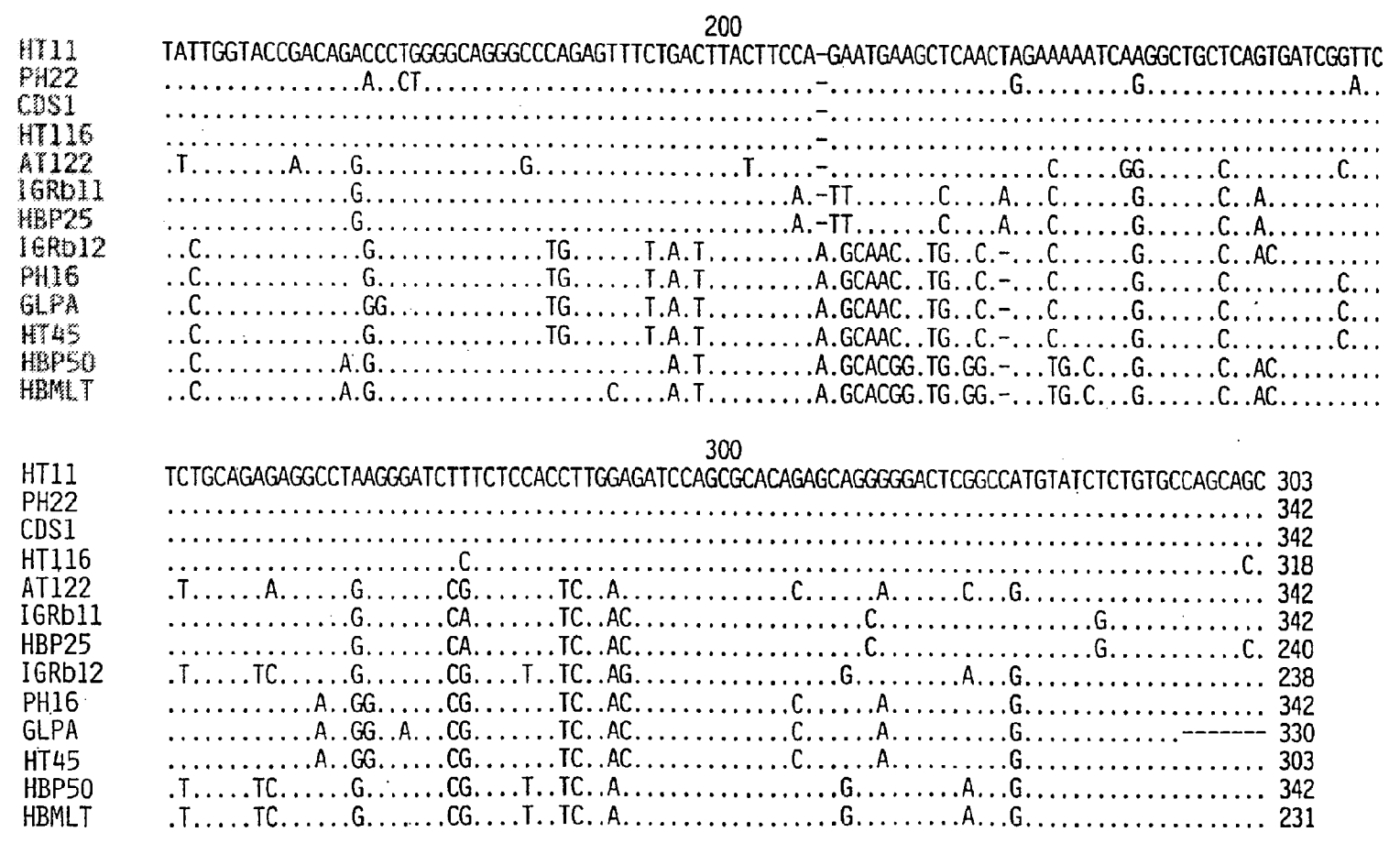

Vβ6 Sub-Family (FIG. 2)

SEQ ID No. 10 (IGR b11)

This sequence corresponds to an extension of the 5' side of clone HBP25 (Kimura, already quoted).

SEQ ID No. 11 (IGR b12)

This sequence which represents a new member shows a similarity of nucleotides of 94% with PH 16 (Tillinghast already quoted), GPPA (Li, already quoted) and HT45 (Kimura (25)).

Vβ12 Sub-Family (FIG. 3)

SEQ ID No. 12 (IGR b13)

This sequence which represents a new member shows a similarity of greater than 85% with the sequences PH27 (Tillinghast already quoted), and PL42 (Concannon, already quoted).

Vβ13 Sub-Family (FIG. 4)

SEQ ID No. 13, 14 and 15 (IGR b14, IGR b15 and IGR b16)

The sequences SEQ ID No. 13 and 14 which represent new members show a similarity of 78 to 91% and 77 to 79% respectively with the other known sequences HBVP34 (Kimura (23)) and CEM (Duby (26)).

The sequence SEQ ID No. 15 show a similarity of 94% with HBVP34. It should be noted that the sequence SEQ ID No. 15 shows an intron (represented by lower case characters) in the leader region. The sequence SEQ ID No. 15 is a consensus sequence. A C instead of a T is observed in position 231 and an A instead of a G is observed in position 259.

Vβ7 Sub-Family (FIG. 5)

SEQ ID No. 16 and 17 (IGR b17 and IGR b18)

These sequences show a strong similarity with the truncated sequence PL4.19 (Concannon, already quoted) and the extension of the 5' side up to the start signal of the translation.

SEQ ID No. 18 (IGR b19)

This sequence extends the sequence PL4.9 (Concannon already quoted) of the 5' side up to the start signal of the translation.

Vβ9 Sub-Family (FIG. 6)

SEQ ID No. 19 (IGR b20)

This sequence extends the sequence PL2.6 (Concannon, already quoted) of the 5' side. A difference between the two sequences is observed in positions 98 and 100 corresponding to different amino acids.

The present invention also aims at providing specific oligonucleotides of different Vβ sub-families, which can be used as primers for the amplification of DNA corresponding to these different Vβ sub-families, with a view, for example, of a study of the expression of certain Vβ sub-families in a patient and finally of a diagnosis of immune disorders, as indicated above.

The predominant expression of certain Vβ sub-families has already been studied using an incomplete range of oligonucleotides.

In this way Sottini et al. (33) have shown, using a range of oligonucleotides, a predominant expression of certain Vβ's in patients suffering from rheumatoid arthritis.

Similarly, Choi Y. et al. (32) have shown, using a range of oligonucleotides, the stimulation of T lymphocytes by *Staphylococcus aureus* toxins by the intermediary of specific Vβ's.

The present invention aims to provide a complete range of oligonucleotides allowing the study, of both known Vβ sub-families and new Vβ sub-families of the invention and which are completely specific to each sub-family. Thus the oligonucleotides have been chosen and synthesized to this end and to the requirements of modifications of one or two nucleotides which have been introduced relative to the natural sequences to reduce the cross-reactions between sub-families.

Thus a subject of the present invention is also oligonucleotides which can be used as primers for the amplification of DNA corresponding to the variable regions of chains of T-cell receptors, chosen form the sequences SEQ ID No. 25 to 48.

Also a subject of the present invention is the use, as primers for the amplification of DNA corresponding to the variable regions of chains of T-cell receptors, of oligonucleotides chosen from the sequences SEQ ID No. 25 to 48.

Also a subject of the present invention is a detection process of nucleotides sequences coding for the V segments of T receptors or of cDNA corresponding to transcription products of the latter, in a biological sample, characterized in that it includes:

a) the amplification of DNA with at least one pair of primers formed by one of the oligonucleotides defined above and one oligonucleotide belonging to a Cβ segment, and b) the detection of amplified sequences with a Cβ probe.

The oligonucleotide belonging to a Cβ segment used for the amplification can be, in particular, chosen from the sequences SEQ ID No. 49 and 50.

To check the efficiency of the amplification, the operation is preferably carried out in the presence of a pair of control primers and the corresponding control sequence amplified using a corresponding control probe is detected.

This pair of control primers can correspond to two Cβ segments, for example the CαE and CαJ primers corresponding to sequences SEQ ID No. 55 and 56. A Cα detection probe (corresponding for example to the sequence SEQ ID NO. 57) is then used. But this pair of primers is advantageously constituted by two primers belonging to β-actin, notably those corresponding to sequences SEQ ID No. 52 and 53. Then a detection probe corresponding to a sequence of β-actin, such as the sequence SEQ ID No. 54, is used.

Also a subject of the present invention is a diagnostic kit for the implementation of the process defined previously, which includes:

a) at least one oligonucleotide chosen from the sequences SEQ ID No. 25 to 48, b) a Cβ primer, c) a Cβ probe.

In addition such a kit advantageously contains:
  d) a pair of control primers,
  e) a control probe.

This kit can contain in particular:
  a) the group of 24 oligonucleotides corresponding to sequences SEQ ID No. 25 to 48,
  b) a Cβ primer chosen from the sequences corresponding to sequences SEQ ID No. 49 and 50,
  c) a pair of control primers for β-actin having a sequence corresponding to sequences SEQ ID NO. 52 and 53 respectively,
  d) a Cβ probe corresponding to the sequence SEQ ID No. 51,
  e) a control probe for β-actin corresponding to the sequence SEQ ID No. 54.

In the information given in the list of sequences for the sequences 25 to 54, the sequences SEQ ID No. 25 to 45 correspond to sequences belonging to clones of known Vβ1 to Vβ20 sub-families (available from the EMBL database) or to sequences which differ from them by one or two nucleotides. The sequences SEQ ID No. 45, 46, 47 and 48 correspond to sequences belonging to clones of new sub-families of the invention, corresponding to sub-families provisionally designated Vβw21, Vβw22, Vβw23 and Vβw24 (w indicating that the designation is pending definitive designation).

The sequences SEQ ID No. 49 and 50 are two examples of Cβ oligonucleotides which can be used as primers for amplification.

The sequence SEQ ID No. 51 is the sequence of a Cβ probe which can be used for the detection of amplified DNAs.

Finally, the sequences SEQ ID No. 52, 53 and 54 are respectively the sequences of a pair of oligonucleotides belonging to the sequence of β-actin which can be used to check the amplification and the sequence of a probe for detecting the corresponding amplified DNAs.

In the list of sequences the position indicated is the position of the 5' end counting from the predicted initiation site of the ATG translation. In the case where the sequences are incomplete (unknown 5' region), the position (marked with an asterisk) is given relative to the first nucleotide of the sequence. The underlined nucleotides correspond to mismatches introduced relative to the natural sequence.

The oligonucleotides were synthesized with an Applied Biosystems 381 A automated DNA synthesizer using the β-cyano-ethylphosphoramidite method (Sinha N. et al. (34)) and following the protocol recommended by the manufacturer. The oligonucleotides were detritylated in the apparatus, cleaved from the support and deprotected with ammonia (at 60° C. for 5 hours). The crude products were purified by inverted phase high pressure chromatography on a μ-bondapak C18 column using an acetonitrile gradient (9 to 15%) in a 0.01M triethylammonium acetate buffer at pH 5.5.

The amplification carried out using the primers according to the invention can be, in particular, the technique of amplification by PCR (Polymerase Chain Reaction) as described by Saiki et al. (14) and in U.S. Pat. Nos. 4,683,195; 4,683,202; 4,889,818.

For the PCR, a double strand DNA can be used which is denatured or a cDNA obtained from RNA using reverse transcriptase as mentioned above.

The polymerization agent is a DNA polymerase, in particular, Taq polymerase.

Generally the amplification cycle is repeated 25 to 40 times.

The probes which are used for detecting the amplified sequences can be obtained by labelling the oligonucleotides with a radio-active isotope, which leads to detection by autoradiography, or by conjugation with an enzyme such as peroxidase (ECL Amersham system), alkaline phosphatase or β-galactosidase (Tropix Ozyme system), which leads to detection by chemiluminescence.

The following example illustrates the implementation of the detection process according to the invention.

The peripheral lymphocytes of a healthy individual were prepared by density gradient centrifugation. The total DNA was extracted according to a one-stage method by extraction with guanidium isothiocyanate, phenol and chloroform (Chomczynski, 13). The complementary DNA was synthesized in a final volume of 20 μl at 42° C. for one hour using 1 to 5 μg of total RNA, the reverse transcriptase and the CβB primer (1.25 uM).

The material obtained was then heated at 95° C. for 3 minutes before being subjected to an amplification according to the PCR technique using in parallel each of the specific VP primers corresponding to sequences SEQ ID No. 25 to 48 and the CβB primer specific to the Cβ region (SEQ ID No. 50). This amplification was carried out in a final volume of 10 μl per tube containing 50 mM of KCl, 10 mM of tris-HCl pH 8.3, 1.5 mM of $MgCl_2$, 0.1% (weight/volume) of gelatine, 200 μM of dNTP, 0.25 units of Taq polymerase and 0.25 μM of each primer. A control amplification was carried out in each tube from 25 mN of a DNA fragment of β-actin of 877 base pairs prepared by PCR and Act 1 and Act 2 primers (SEQ ID No. 52 and 53) specific to actin. 30 amplification cycles were carried out followed by a final elongation stage of 5 minutes at 72° C. Each cycle included a denaturation stage at 94° C. for one minute, a hybridization stage at 65° C. for one minute and an elongation period at 72° C. for one minute.

The products obtained were separated by electrophoresis on 2% agarose gel, transferred onto nylon membranes in an alkaline buffer and hybridized simultaneously with the CβC oligonucleotide probes (SEQ ID No. 51) and Act 3 (SEQ ID No. 54) labelled with $32_P$ by the polynucleotidyl T4 kinase enzyme. The hybridization was carried out at 42° C. for 16 hours in a buffer containing 6×SSC, 0.5% SDS, 5×Denhardt's, 0.05% $NaH_2PO_4$ and 100 μg/ml of denatured salmon sperm DNA. The membranes were then washed with SSC 6×, 20 mM $NaH_2PO_4$, twice at ambient temperature for 5 minutes and once at 50° C. for 30 minutes then autoradiographed.

Figure 8:
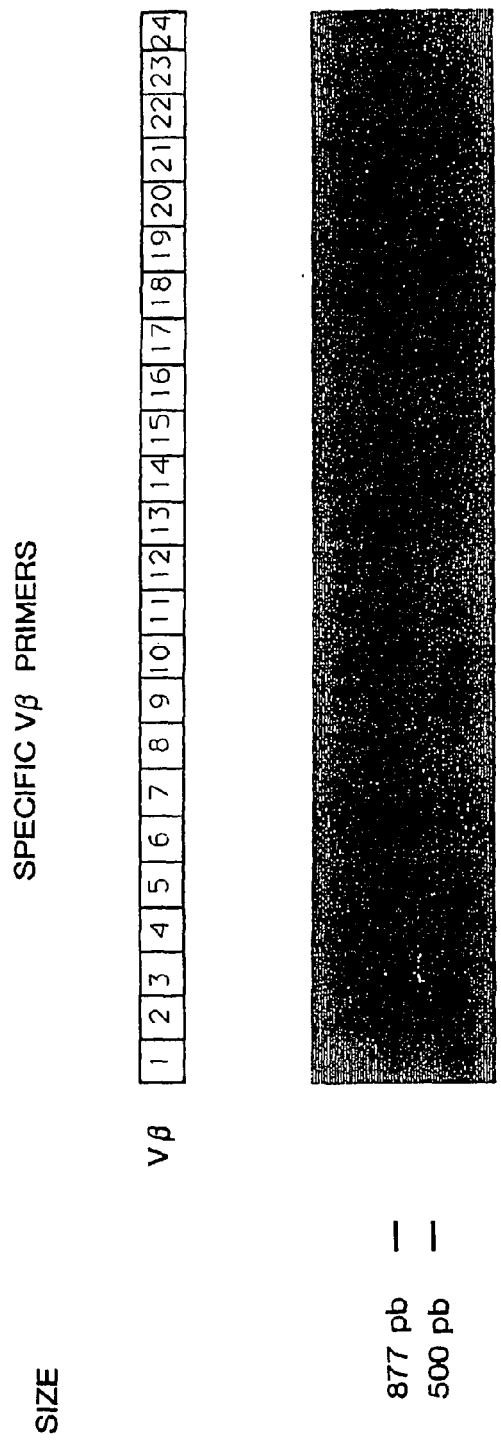
FIG. 8 represents the detection by autoradiography of amplified transcripts of TCRβ chains expressed by the peripheral lymphocytes of a healthy individual and of a co-amplified β-actin control.

The results obtained are shown in FIG. 8.

The actin control (band of 877 base pairs) allows the amplification to be verified in all wells. A specific signal appears below this band the size of which corresponds to the size of corresponding amplified fragments, each fragment having a length corresponding to the distance between the locus of the specific Vβ oligonucleotide and the Cβ primer.

With the individual tested, FIG. 8 shows the preferential expression of certain genetic segments defined relative to the others. For example, the Vβ1 and 2 sub-families are more represented than the other sub-families.

Example of the Preparation of Anti V 13 Monoclonal Antibodies: RO-73 and JU-74 Monoclonal Antibodies 1) Immunizing Cells The clone T 3025 (Moebius et al. (35)) was cultivated in complete medium containing DMEM (Seromed), 8% AB human serum, IL-2 and TCGF as described by Hercend et al. (36). Periodic restimulations were carried out on allogenic cells in the presence of IL-2. The messenger RNAs coding for the T receptor expressed by these cells were sequenced using the A-PCR technique and represent rearrangements of genetic segments Vα10 (sequence HAP58, Yoshikai et al. (37)) and Vβ13 (sequence IGRb16=SEQ ID No. 15 indicated above).

2) Immunization of Mice 6-week old Biozzi mice (Curie Institute, Paris, France) were immunized with whole T cells of clone 3025. After a first intraperitoneal injection of 5×10⁶ cells in Freund's complete adjuvant, the mice received three intraperitoneal injections of 5×10⁶ cells in Freund's incomplete adjuvant at three-week intervals. Two weeks after the last intra-peritoneal injection the mice received an intravenous injection of 2×10⁶ viable cells. The mice were killed three days later and the spleen was removed.

3) Fusion

The fusion of spleen cells with the myeloma which does not secrete NS-1 was carried out according to the Kohler and Milstein method (38). The NS-1 cells (Kohler and Milstein (39)) were cultivated in a medium containing DMEM (Seromed), 8-azaguanine (Sigma, Saint Louis, Mich.), 10% horse serum (Seromed, lot No. 5Z04), penicillin and streptomycin (Eurobio), glutamine (Seromed, 200 mM) and sodium pyruvate (Gibco, 100 mM).

The splenocytes were fused with NS-1 cells with polyethylene-glycol (PEG 1000, Merck) in a ratio of 4 spleen cells per one myeloma cell. After the fusion, the cells were cultivated at 3×10⁶ cells per ml in plates of 96 wells (Nunc) in a HAT selection medium containing DMEM, 10% horse serum, 10% fetal calf serum (Seromed, lot No. 219195), aminopterin (Gibco), hypoxanthine and thymidine (Gibco), penicillin and streptomycin, glutamine, sodium pyruvate and NCTC 109 (Eurobio). Fresh medium was added to the wells 2 days (50 µl per well) and 9 days (100 µl per well) after fusion. The culture was carried out at 37° C., in an incubator containing 10% $CO_2$.

4) Screening of Hybridomas

The supernatant of hybridomas obtained was collected 15 days after fusion and its reactivity was tested with the immunizing cell by indirect immunofluorescence and analysed by flow cytometry analysis. In brief, the T3025 cells were incubated at 4° C. for 30 minutes with the hybridoma supernatant (100 µl per 300,000 cells), washed and labelled with a mouse anti-immunoglobulin goat antibody conjugated with fluorescein (Coulter Electronics, Hialeah, Fla.). The cells were then analyzed by flow cytometry analysis. (Coulter Profile). As is shown in FIGS. 9A and 10A, the supernatants of hybridomas RO-73 and JU-74 allow the labelling of 100% of the cells of immunizing clone 3025. An anti-CD3 antibody (OKT3 Ortho-Co) and the anti-clono-type NKTa antibody (IgG1, Hercend et al (40)) served respectively as positive and negative controls in this experiment.

The anti-T receptor specificity of the monoclonal antibodies was analyzed according to the following criteria:

1—the antibodies must recognize the immunizing T clone 3025 but not a T clone carrying a different T-cell receptor (TCR), for example the clone 12410 (Moebius et al., (35) expressed TCR: $V\alpha3/V\beta17$).

2—The antibodies must react with a low percentage of circulating lymphocytes (PBL).

3—The structure of the surface recognized by the antibodies on the immunizing cell must co-modulate with the CD3 molecule at the time of the incubation of the cells in the presence of anti-CD3 antibodies (Meuer et al. (1)).

As FIGS. 9 and 10 show, the supernatants of hybridomas RO-73 and JU-74 react with 100% of the cells of immunizing clone 3025 (FIGS. 9A and 10A), less than 2% of the cells of clone 12410 (FIGS. 9B and 10A) and 1 to 3% of the PBLs (FIGS. 9C and 10C).

For the co-modulation experiments, the cells of clone 3025 (10⁶ cells per ml) were incubated in medium only or in the presence of anti-CD3 antibodies (OKT3) in 24-well culture plates. After incubation for 24 hours the cells were collected and labelled with the supernatant of hybridoma RO-73 or JU-74, anti-CD3 monoclonal antibody or an anti-CD2 control monoclonal antibody (Coultronics Co.) then analyzed by flow cytometry analysis. As FIGS. 11 and 12 show, the flow cytometry analysis of cells incubated in the presence of anti-CD3 monoclonal antibody (FIGS. 11B and 12B) shows a diminution of the fluorescence intensity for the anti-CD3 monoclonal antibody as well as for RO-73 and JU-74, while the labelling intensity with anti-CD2 monoclonal antibody increases in comparison to the intensity obtained respectively in the absence of anti-CD3 antibody (FIG. 11A and FIG. 11B). These results indicate that the molecule recognized by the RO-73 and JU-74 antibodies co-modulates with the CD3 molecule at the surface of the cells of clone T 3025.

6) Isolation of a Sub-Clone

The cells of the initial hybridomas, respectively RO-73 and JU-74 were distributed on culture plates at the rate of 0.5 cell per well in complete HAT medium, on irradiated syngeneic spleen cells. Three sub-clones were selected for each of the hybridomas RO-73 and JU-74. These cells produce monoclonal antibodies whose reactivity is identical to that of the initial hybridomas (results not shown).

The sub-clones were cultivated in non-selective medium containing DMEM, 10% fetal calf serum, 10% horse serum, hypoxanthine, thymidine, penicillin and streptomycin, glutamine, sodium pyruvate and NCTC 109.

The cells of the hybridomas or sub-clones were frozen in fetal calf serum containing 10% of dimethyl sulphoxide (DMSO, Merck) and stored in liquid nitrogen.

7) Isotyping of Monoclonal Antibodies

The isotypes were determined by immunodiffusion on a solid support using an "INNO-LIA mouse mAb isotyping" kit (Innogenetics) for the determination of the isotypes of immunoglobulins in the supernatants of the culture. RO-73 and JU-74 are mouse immunoglobulins of isotype IgG1, kappa.

8) Purification of Monoclonal Antibodies

Ascites were produced in nude mice. The ascitic liquid obtained was filtered through cotton to eliminate the fibrin and precipitated with sodium sulphate (18%). The deposit obtained was suspended in PBS buffer, ⅓ diluted in a buffer (NaCl 4.5M, Glycine 2.25M, pH 8.8) and loaded into a column of Protein A-Sepharose 4 Fast Flow equilibrated in the loading buffer (NaCl 3M, glycine 1.5M, pH 8.8). A major peak of immunoglobulins was eluted at pH 6 using successive elution buffers of decreasing pH. This major peak was purified on an ion exchange column (Q Sepharose Fast Flow) in a Tris 50 mM, pH 8 buffer and eluted with an NaCl gradient.

The purity of the preparation was verified by electrophoresis in a PHAST system (Pharmacia LKB, Uppsala, Sweden) and the purified immunoglobulins were tested by indirect immuno-fluorescence on the cell 3025, as indicated previously.

As an example, for 30 ml of ascite of the hybridoma RO-73, 32 mg of purified immunoglobulins was obtained after purification on Protein A and Q Sepharose Fast Flow.

9) Percentage of PBL Recognized by the Monoclonal Antibodies

The percentage of circulating lymphocytes recognized respectively by the monoclonal antibodies RO-73 and JU-74 was determined for 10 different healthy donors. The results are shown in Table 1. The monoclonal antibody JU-74 recognizes less than 0.5% to 2.1% of the PBLs (average 1.08%) and the monoclonal antibody RO-73 recognizes from 0.5% to 2.2% of the PBLs according to the individuals (average 1.09%). For a given individual, the monoclonal antibodies RO-73 and JU-74 recognize respectively approximately the same percentages of circulating lymphocytes.

TABLE 1

Reactivity of monoclonal antibodies RO-73 and JU-74 with peripheral blood cells

| Donor | RO-73 | JU-74 |
|---|---|---|
| BQ | 2.2 | 2.1 |
| BY | 0.9 | 1.1 |
| BZ | <0.5 | <0.5 |
| CA | 0.5 | <0.5 |
| CB | 0.5 | 0.6 |
| CD | 1.8 | 1.7 |
| CE | 0.4 | 0.3 |
| CH | 1.6 | 1.3 |
| CI | 1.4 | 1.2 |
| CJ | 1.1 | 1.5 |

10) Purification of PBLs Recognized by the Monoclonal Antibodies

The PBLs recognized respectively by the monoclonal antibodies RO-73 and JU-74 were purified from a normal donor using a positive selection process with magnetic beads (Dynabeads, Dynal). In brief, 1 to $4\times10^9$ PBL were labelled by one or other of the above purified monoclonal antibodies and incubated with ready to use Dynabeads M-450 beads covered with a mouse anti-IgG goat serum, in the proportion of 3 beads per labelled cell. The positive cells were then separated using a magnet. After several washings, the cells were incubated with an excess of mouse anti-IgG goat immunoglobulins ("Detach-a-beads", Dynatech) in order to detach the magnetic beads then directly analyzed by flux cytometry analysis after labelling with the monoclonal antibody RO-73 or the monoclonal antibody JU-74, respectively.

The selected positive cells were cultivated in a microplate in the presence of IL-2 on the irradiated allogenic cells then purified again with magnetic beads after culturing for about a week in order to obtain a preparation with a purity greater than 95%.

For the monoclonal antibody JU-74, $8\times10^6$ positive cells of 96% purity were obtained, after a one-week culture, from $1\times10^9$ PBL from a healthy donor containing initially 1.7% of JU-74+ cells.

For the monoclonal antibody RO-73, $9\times10^6$ positive cells of 98% purity were obtained, after a 10-day culture, from $1.2\times10^9$ PBL from a healthy donor containing initially 2.4% of RO-73+ cells.

From the purified RO-73+ and JU-74+ cells selected in this way, the respective cell lines were established; each line is 100% recognized by the two monoclonal antibodies, which shows that the two monoclonal antibodies recognize the same cells in peripheral blood.

Analysis of TCR transcripts expressed in the PBLs recognized by RO-73 and JU-74 by PCR techniques a) Method of Analysing the β Transcripts The range of specific oligonucleotides of vβ segments of type Vβ1 to Vβ24 described above (SEQ ID No. 25 to No. 48) were used as specific primers for analysing the TCRβ transcripts expressed in the RO-73+ and JU-74+ cells. The procedure used is identical to that described in the example above for the peripheral lymphocytes of a healthy individual. In brief, after preparation of the RNA according to the Chomczynski method (13), the complementary DNA was synthesized using reverse transcriptase and the Cβ B primer (SEQ ID No. 50). The material obtained was subjected to 30 amplification cycles according to the PCR technique using in parallel each of the specific Vβ primers corresponding to the sequences SEQ ID No. 25 to 48 and the specific Cβ B primer of the Cβ region (SEQ ID No. 50) as described previously.

The amplified products obtained were separated by electrophoresis on 2% agarose gel, transferred onto nylon membranes and hybridized with the Cβ C oligonucleotide probe (SEQ ID No. 51) labelled with $32_P$. The membranes were then washed as described above then autoradiographed.

The sequencing of the transcripts of the TCR β chain was carried out following the cloning and sequencing method described previously for the cDNA. For example, the material amplified by the specific oligonucleotide of the Vβ 13 subfamily (SEQ ID No. 37) was digested by the enzyme SacII and purified by electrophoresis on agarose gel. The material obtained was introduced into the pBS SK$^+$ vector (as described above for the A-PCR technique) and used to transfect the E. Coli XL-1 blue bacteria. The transformed colonies obtained were tested by dot-blot hybridization using the Cβ C oligonucleotide probe (SEQ ID NO. 51) labelled with $32_P$. The plasmid DNA was sequenced as described previously.

b) Method of Analysing the α Transcripts

A methodology resembling that described for the P transcripts was applied to the analysis of the transcripts of the TCR α chain using as specific primers a range of specific oligonucleotides of V α segments of the Vα1 to Vα29 type and specific oligonucleotides of the constant Cα region (CαB oligonucleotide for the synthesis of the complementary DNA and the amplification by PCR and CαC oligonucleotide for the detection probe). The sequences of these oligonucleotides are indicated in Table 2.

TABLE 2

| Sequence | Type | | |
|---|---|---|---|
| 5'-GGCATTAACGGTTTTGAGGCTGGA-3' | Vα1 | SEQ ID NO: | 58 |
| 5'-CAGTGTTCCAGAGGGAGCCATTGC-3' | Vα2 | SEQ ID NO: | 59 |
| 5'-CCGGGCAGCAGACACTGCTTCTTA-3' | Vα3 | SEQ ID NO: | 60 |
| 5'-TTGGTATCGACAGCTTCCCTCCCA-3' | Vα4 | SEQ ID NO: | 61 |
| 5'-CGGCCACCCTGACCTGCAACTATA-3' | Vα5 | SEQ ID NO: | 62 |
| 5'-TCCGCCAACCTTGTCATCTCCGCT-3' | Vα6 | SEQ ID NO: | 63 |
| 5'-GCAACATGCTGGCGGAGCACCCAC-3' | Vα7 | SEQ ID NO: | 64 |
| 5'-CATTCGTTCAAATGTGGGCAAAAG-3' | Vα8 | SEQ ID NO: | 65 |
| 5'-CCAGTACTCCAGACAACGCCTGCA-3' | Vα9 | SEQ ID NO: | 66 |
| 5'-CACTGCGGCCCAGCCTGGTGATAC-3' | Vα10 | SEQ ID NO: | 67 |
| 5'-CGCTGCTCATCCTCCAGGTGCGGG-3' | Vα11 | SEQ ID NO: | 68 |
| 5'-TCGTCGGAACTCTTTTGATGAGCA-3' | Vα12 | SEQ ID NO: | 69 |
| 5'-TTCATCAAAACCCTTGGGGACAGC-3' | Vα13 | SEQ ID NO: | 70 |
| 5'-CCCAGCAGGCAGATGATTCTCGTT-3' | Vα14 | SEQ ID NO: | 71 |
| 5'-TTGCAGACACCGAGACTGGGGACT-3' | Vα15 | SEQ ID NO: | 72 |
| 5'-TCAACGTTGCTGAAGGGAATCCTC-3' | Vα16 | SEQ ID NO: | 73 |
| 5'-TGGGAAAGGCCGTGCATTATTGAT-3' | Vα17 | SEQ ID NO: | 74 |
| 5'-CAGCACCAATTTCACCTGCAGCTT-3' | Vα18 | SEQ ID NO: | 75 |
| 5'-ACACTGGCTGCAACAGCATCCAGG-3' | Vα19 | SEQ ID NO: | 76 |
| 5'-TCCCTGTTTATCCCTGCCGACAGA-3' | Vα20 | SEQ ID NO: | 77 |

TABLE 2-continued

| Sequence | Type | |
|---|---|---|
| 5'-AGCAAAATTCACCATCCCTGAGCG-3' | Vα21 | SEQ ID NO: 78 |
| 5'-CCTGAAAGCCACGAAGGCTGATGA-3' | Vα22 | SEQ ID NO: 79 |
| 5'-TGCCTCGCTGGATAAATCATCAGG-3' | Vαw23 | SEQ ID NO: 80 |
| 5'-CTGGATGCAGACACAAAGCAGAGC-3' | Vαw24 | SEQ ID NO: 81 |
| 5'-TGGCTACGGTACAAGCCGGACCCT-3' | Vαw25 | SEQ ID NO: 82 |
| 5'-AGCGCAGCCATGCAGGCATGTACC-3' | Vαw26 | SEQ ID NO: 83 |
| 5'-AAGCCCGTCTCAGCACCCTCCACA-3' | Vαw27 | SEQ ID NO: 84 |
| 5'-TGGTTGTGCACGAGCGAGACACTG-3' | Vαw28 | SEQ ID NO: 85 |
| 5'-GAAGGGTGGAGAACAGATGCGTCG-3' | Vαw29 | SEQ ID NO: 86 |
| 5'-ATACACATCAGAATTCTTACTTTG-3' | CαA | SEQ ID NO: 87 |
| 5'-GTTGCTCCAGGCCGCGGCACTGTT-3' | CαB | SEQ ID NO: 88 |
| 5'-GTCACTGGATTTAGAGTCT-3' | CαC | SEQ ID NO: 57 | c) Results

FIG. 13 shows the results obtained for the analysis of transcripts of TCR α chains (FIG. 13A) and β chains (FIG. 13B) expressed by the RO-73+ cells recognized by the monoclonal antibody RO-73. It should be noted that numerous different Vα segments are expressed in these cells (FIG. 13A). On the other hand, only the specific oligonucleotide of the sequences of the Vβ13 sub-family allows an amplification of the cDNA (FIG. 13B).

Identical results were obtained for the TCRβ transcripts expressed in the JU-74+ cells recognized by the monoclonal antibody JU-74 (results not shown).

In addition, the β transcripts which correspond to the Vβ13 sub-family expressed by the JU-74+ cells were sequenced from cells previously isolated in order to determine, among the 5 known or new members of the Vβ13 sub-family (FIG. 4), those whose products are recognized by the monoclonal antibody JU-74. Table 3 shows the results obtained after analysis of these sequences. The eight different sequences of Vβ13 obtained all correspond to a rearrangement of the new Vβ13 genetic segment IGRb16 (SEQ ID No. 15) with different J segments and N regions.

TABLE 3

Expression of the transcripts of the β chain in JU-74+ cells

| cDNA clones | Vβ | member | Jβ | Region N |
|---|---|---|---|---|
| B001 | 13 | IGRb16I | J2.1 | + |
| B002 | 13 | IGRb16I | J1.6 | + |
| B006 | 13 | IGRb16I | J1.1 | + |
| B007 | 13 | IGRb16I | J2.1 | + |
| B009 | 13 | IGRb16I | J1.6 | + |
| B010 | 13 | IGRb16I | J2.6 | + |
| B011 | 13 | IGRb16I | J1.3 | + |
| B012 | 13 | IGRb16I | J1.2 | + |

All these results show that the monoclonal antibodies RO-73 and JU-74 are specific to products of genetic segments belonging to the Vβ13 sub-family.

More precisely, the monoclonal antibodies JU-74 and RO-73 have the same specificity and recognize exclusively the product of the new Vβ13 genetic segment IGRb16 of the invention. (SEQ ID No. 15 indicated above).

The following hybridoma cell lines were deposited with the Collection Nationale de Culture de Microorganismes (CNCM Pasteur Institute): JU-74 and RO-73 on the 12 Feb. 1992 under the numbers I-1173 and I-1172.

REFERENCES

1. Meuer, S. C., et al., J. Exp. Med. 1983. 157:705.
2. Moingeon, P., et al., Nature 1986a. 323:638.
3. Brenner, M. B., et al., Nature 1986. 322:145.
4. Bank, I., et al., Nature 1986. 322:179.
5. Davis, M. M., et al., Nature 1988. 334:395.
6. Crews, S., et al., Cell 1981. 25:59.
7. Wilson, R. K., et al., Immunological Reviews 1988c. 101: 149.
8. Robinson, M. A., Proc. Natl. Acad. Sci. USA 1989. 86:9422.
9. Leiden, J. M., et al., Proc. Natl. Acad. Sci. USA 1986. 83:4456.
10. Reynolds 1986.
11. Li, Y., et al., J. Exp. Med. 1990. 171:221.
12. Chirgwin, J. M., et al. Biochemistry 1979. 18:5294.
13. Chomczynski, P., et al., Anal. Biochem. 1987. 162:156.
14. Saiki, R. K., et al., Science 1988. 239:487.
15. Loh, E. Y., et al., Science 1989. 243:217.
16. Sanger, F., et al., Proc. Natl. Acad. Sci. USA 1977. 74:5463.
17. Lipman, D. J., et al., Science 1985. 227:1435.
8. Kozak, M., Nucl. Acids Res. 1984. 12:857.
19. Kyte, J., et al., R. F., J. Mol. Biol. 1982. 157:105.
20. Triebel, F., et al., J. Immun. 1988. 140:300.
21. Feinberg, A. P., et al., Anal. Bichem. 1983. 132:6.
22. Tillinghast, J. P., et al., Science 1986. 248:879.
23. Kimura, N., et al., J. Exp. Med. 1986. 164:739.
24. Concannon, P., et al., Proc.
25. Kimura, N., et al., Eur. J. Immunol. 1987. 17:375.
26. Duby, A. D., et al., Proc. Natl. Acad. Sc. USA 1986. 83:4890.
27. Naudenbark, A., et al., Nature, 341, 541.
28. Janeway, C., Nature, 341, 482.
29. Lin, Y., J. Exp. Med., 171, 221.
30. Acha-Orbea, H., EMBO Journal, 1990, 9, 12, 3815.
31. Kappler, J., Science 244, 811.
32. Choi, Y., PNAS, 86, 8941.
33. Gottini A. et al., Eur. J. Immunol., 1991, 21, 461.
34. Sinha N. et al., Nucleic Acids Res. 1984, 12, 4539.
35. Moebius, U. et al., Eur. J. Immunol. 1990, 20, 889.
36. Hercend, T. et al., Cellular Immunol., 1984, 86, 381.
37. Yoshikai, Y. et al. J. Exp. Med., 1986, 164, 90.
38. Kohler, G. and Milstein, C., Nature, 1975, 256, 495.
39. Kohler, G. and Milstein, C., Eur. J. Immunol., 1976, 6, 511.
40. Hercend, T. et al., J. Exp. Med., 158, 1983, 1547.
41. Wilson, R. K. et al., Immunogenetics, 1990, 32, 406.

The invention claimed is:

1. An isolated antibody, or an antigen binding fragment thereof, directed against an antigenic determinant of a Vβ peptide encoded by a nucleic acid sequence selected from the group consisting of:
   nucleotides 54 to 395 of SEQ ID NO: 3,
   nucleotides 18 to 329 of SEQ ID NO: 4, and
   nucleotides 28 to 366 of SEQ ID NO: 5,
wherein the antibody, or antigen binding fragment thereof, specifically binds to the Vβ peptide.

2. The antibody or an antigen binding fragment of claim 1, which is a monoclonal antibody or an antigen binding fragment thereof.

3. The antigen binding fragment of claim 2, wherein the fragment is selected from the group consisting of a Fab fragment, a Fab' fragment, and a (Fab')$_2$ fragment.

4. A diagnostic composition comprising the monoclonal antibody of claim 2.

5. A diagnostic composition comprising the antigen binding fragment of claim 3.

6. A therapeutic composition comprising the monoclonal antibody of claim 2.

7. A therapeutic composition comprising the antigen binding fragment of claim 3.

8. The therapeutic composition of claim 6, wherein the composition further comprises a cytotoxic molecule or a radio-isotope.

9. The therapeutic composition of claim 7, wherein the composition further comprises a cytotoxic molecule or a radio-isotope.

10. A composition comprising the monoclonal antibody or antigen binding fragment of claim 2, and one or more anti-CD3 antibodies.

11. A composition comprising the antigen binding fragment of claim 3, and one or more anti-CD3 antibodies.

* * * * *